(12) United States Patent
Samsoondar

(10) Patent No.: US 9,658,242 B2
(45) Date of Patent: May 23, 2017

(54) AUTOMATED ULTRA-FILTRATION APPARATUS

(71) Applicant: ChroMedX Corp., Toronto (CA)

(72) Inventor: James Samsoondar, Markham (CA)

(73) Assignee: CHROMEDX CORP., Toronto, Ontario (CA)

( * ) Notice: Subject to any disclaimer, the term of this patent is extended or adjusted under 35 U.S.C. 154(b) by 75 days.

(21) Appl. No.: 14/725,690

(22) Filed: May 29, 2015

(65) Prior Publication Data
US 2015/0260747 A1   Sep. 17, 2015

Related U.S. Application Data

(63) Continuation of application No. PCT/CA2013/050935, filed on Dec. 6, 2013.

(Continued)

(51) Int. Cl.
*B01D 61/14* (2006.01)
*B01L 99/00* (2010.01)
(Continued)

(52) U.S. Cl.
CPC ......... *G01N 35/1083* (2013.01); *B01D 61/20* (2013.01); *B01D 61/22* (2013.01);
(Continued)

(58) Field of Classification Search
CPC .... B01D 61/14; B01D 63/02; B01D 2313/44; B01D 2313/16; B01D 2313/58;
(Continued)

(56) References Cited

U.S. PATENT DOCUMENTS 3,753,657 A   8/1973   Downing et al.
4,474,071 A   10/1984   Marteau d'Autry
(Continued)

FOREIGN PATENT DOCUMENTS

WO   93/20440 A1   10/1993
WO   2013165594   11/2013

OTHER PUBLICATIONS

Office Action issued in connection with related Canadian Patent Application No. 2,870,368 dated Apr. 16, 2015.
(Continued)

*Primary Examiner* — Paul Hyun
(74) *Attorney, Agent, or Firm* — Bereskin & Parr LLP/S.E.N.C.R.L., s.r.l.; Ian C. McMillan

(57) ABSTRACT

The present invention provides a disposable ultra-filtration system comprising a disposable pipetting tip and a disposable ultra-filtration cartridge, wherein the cartridge includes a membrane filtration chamber and a dead-end channel. In use, a piston in the pipette pressurizes air within the channel; the pressurized air can subsequently move the piston and cause a reverse flow back through the membrane of the cartridge, unplugging the pores thereof. Also disclosed is an automated workstation incorporating the disposable ultra-filtration system, and a system comprising the automated workstation, useful for measuring the free therapeutic drug concentration and free hormone concentration in a sample.

11 Claims, 14 Drawing Sheets

Related U.S. Application Data

(60) Provisional application No. 61/735,041, filed on Dec. 9, 2012.

(51) Int. Cl.
  *B01D 27/00* (2006.01)
  *G01N 35/10* (2006.01)
  *B01D 61/20* (2006.01)
  *G01N 33/49* (2006.01)
  *B01D 63/02* (2006.01)
  *B01D 65/02* (2006.01)
  *B01D 61/22* (2006.01)
  *B01L 3/02* (2006.01)
  *G01N 33/74* (2006.01)
  *G01N 33/94* (2006.01)
  *G01N 35/00* (2006.01)

(52) U.S. Cl.
  CPC ............. *B01D 63/02* (2013.01); *B01D 65/02* (2013.01); *B01L 3/0237* (2013.01); *B01L 3/0279* (2013.01); *G01N 33/491* (2013.01); *G01N 33/74* (2013.01); *G01N 33/94* (2013.01); *G01N 35/00732* (2013.01); *B01D 2313/16* (2013.01); *B01D 2313/44* (2013.01); *B01D 2313/58* (2013.01); *B01D 2321/04* (2013.01); *B01L 2300/0663* (2013.01); *B01L 2300/0681* (2013.01); *B01L 2400/0478* (2013.01); *G01N 2035/00475* (2013.01); *G01N 2035/00752* (2013.01); *G01N 2035/00811* (2013.01); *G01N 2035/103* (2013.01); *G01N 2035/1053* (2013.01)

(58) Field of Classification Search
  CPC .. G01N 2035/1053; G01N 2035/00475; B01L 2300/0681
  See application file for complete search history.

(56) References Cited

U.S. PATENT DOCUMENTS

| | | |
|---|---|---|
| 4,744,071 A | 5/1988 | Bricot et al. |
| 5,658,800 A | 8/1997 | Lessard et al. |
| 6,444,171 B1 | 9/2002 | Sakazume et al. |
| 7,141,213 B1 | 11/2006 | Pang et al. |
| 7,807,450 B2 | 10/2010 | Samsoondar |
| 7,816,124 B2 | 10/2010 | Samsoondar |
| 2006/0175242 A1* | 8/2006 | Dorian ................ A61M 1/0281 210/321.68 |
| 2009/0220379 A1 | 9/2009 | Wakamiya et al. |
| 2011/0151577 A1 | 6/2011 | Zhang et al. |
| 2011/0287447 A1 | 11/2011 | Norderhaug et al. |
| 2011/0300621 A1 | 12/2011 | Belz et al. |
| 2013/0026085 A1 | 1/2013 | Samsoondar |

OTHER PUBLICATIONS

Office Action issued in connection with related Canadian Patent Application No. 2,870,368 dated Feb. 9, 2015.
Office Action issued in connection with related Canadian Patent Application No. 2,870,368 dated Jan. 22, 2015.
Voluntary Amendment submitted in connection with related Canadian Patent Application No. 2,870,368 dated Jan. 22, 2015.
Office Action issued in connection with related Canadian Patent Application No. 2,870,368 dated Nov. 27, 2014.
Office Action issued in connection with related Canadian Patent Application No. 2,876,445 dated May 1, 2015.
Voluntary Amendment submitted in connection with related Canadian Patent Application No. 2,876,445 dated Feb. 9, 2015.
Office Action issued in connection with related Canadian Patent Application No. 2,876,602 dated May 1, 2015.
Voluntary Amendment submitted in connection with related Canadian Patent Application No. 2,876,602 dated Feb. 9, 2015.
Office Action issued in connection with related Canadian Patent Application No. 2,876,602 dated Feb. 3, 2015.
International Preliminary Report on Patentability issued in connection with related International Patent Application No. PCT/CA2013/050935 dated Mar. 24, 2015.
Written Opinion issued in connection with related International Patent Application No. PCT/CA2013/050935 dated Oct. 28, 2014.
Response to Written Opinion submitted in connection with related International Patent Application No. PCT/CA2013/050935 dated Sep. 25, 2014.
International Search Report and Written Opinion issued in connection with related International Patent Application No. PCT/CA2013/050935 dated Apr. 2, 2014.
Extended European Search Report (EESR) for corresponding EP Application No. 13859916.2, dated Jul. 20, 2016.

\* cited by examiner

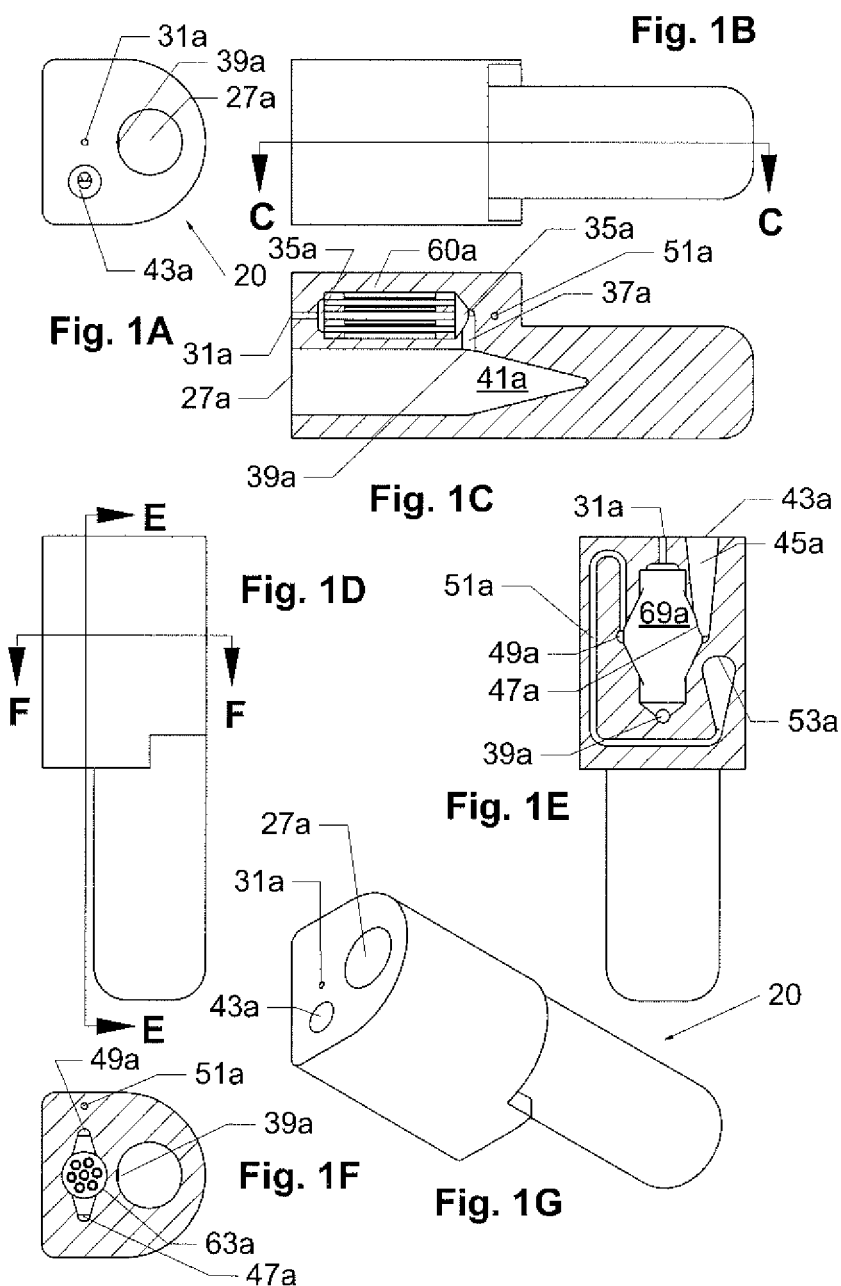

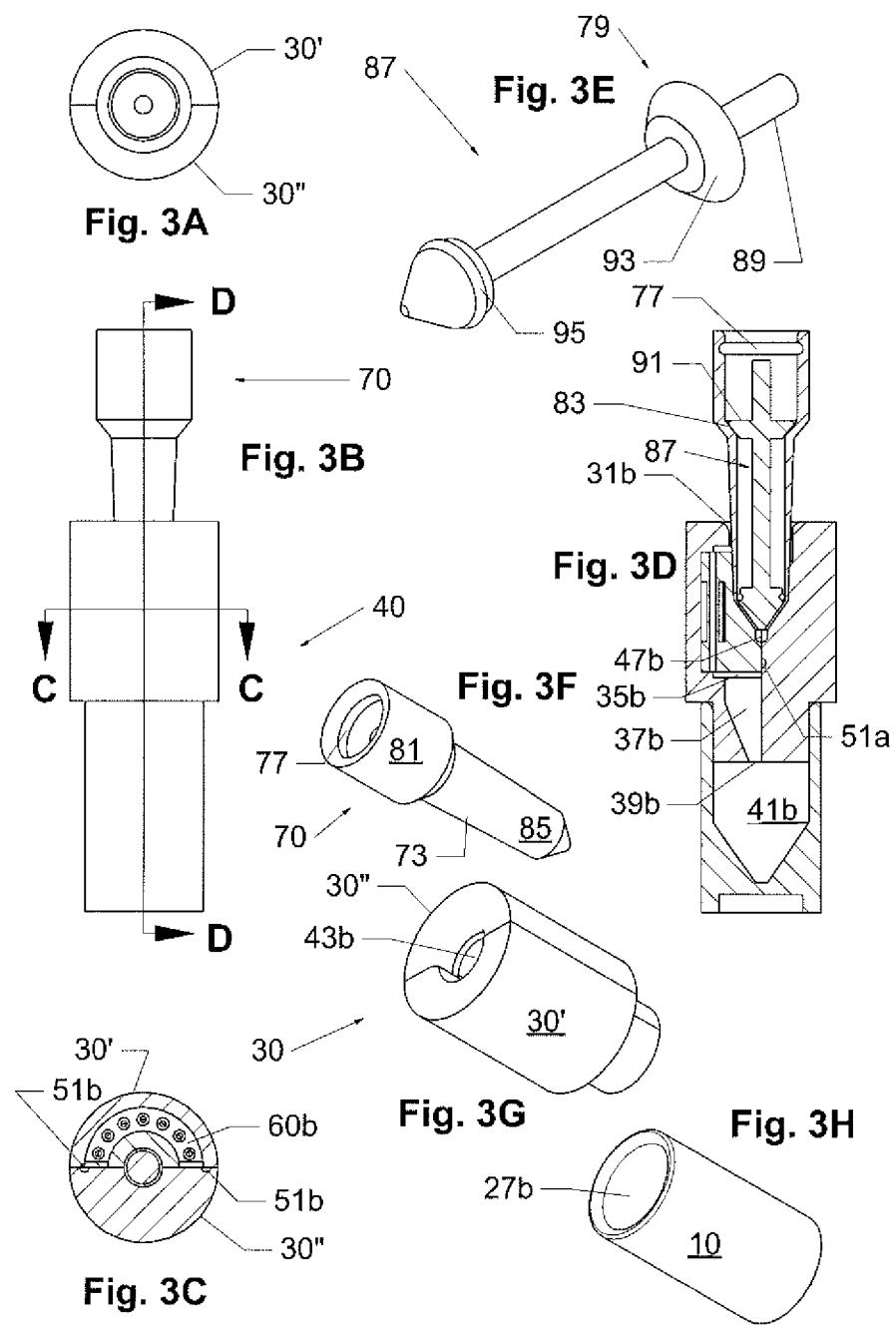

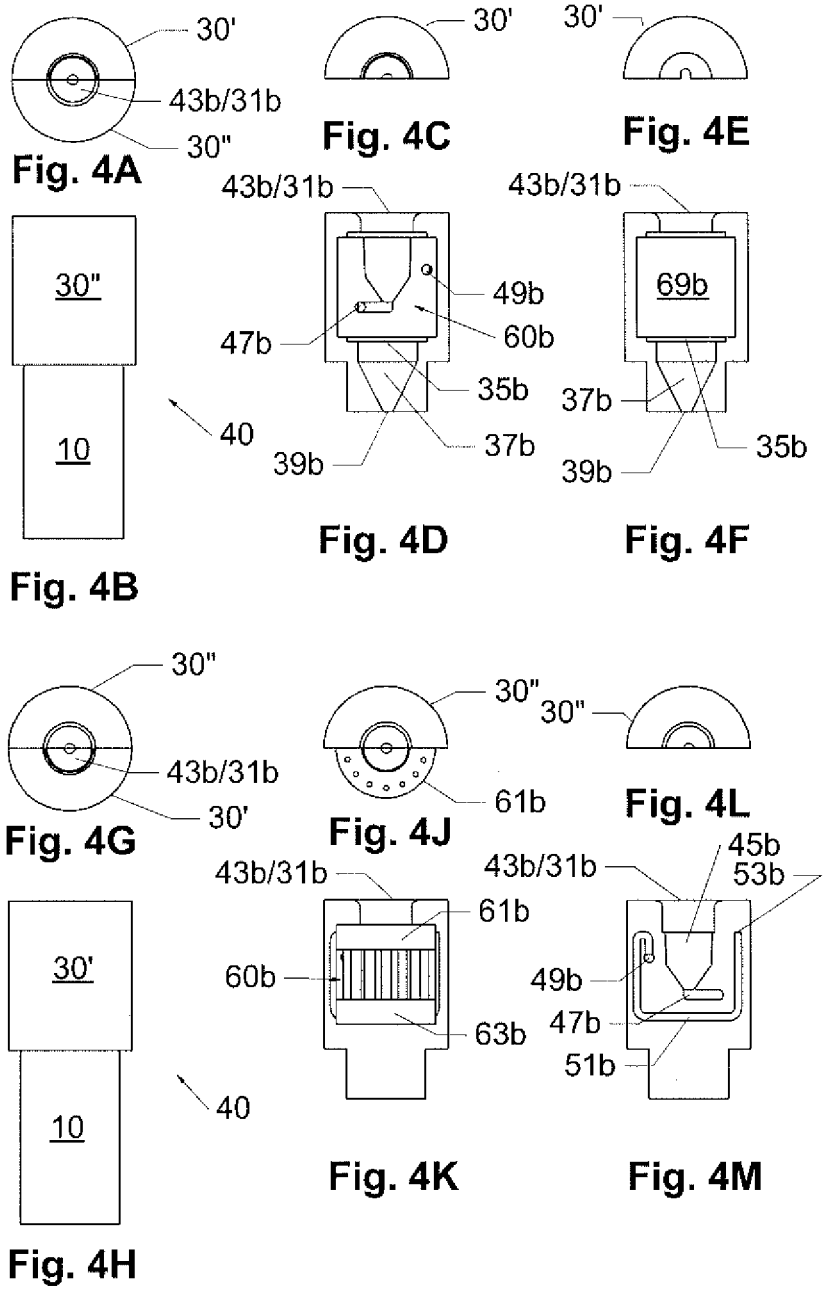

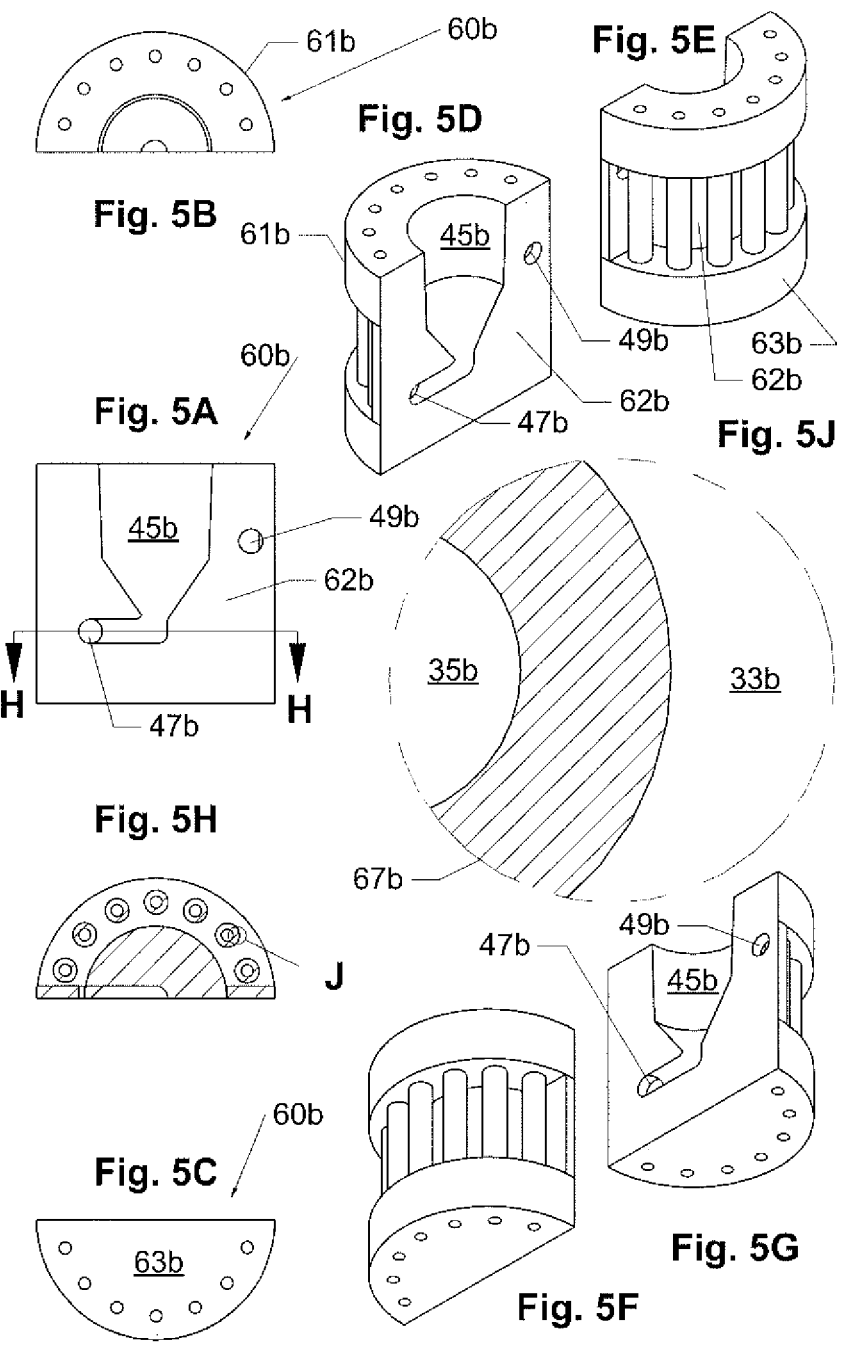

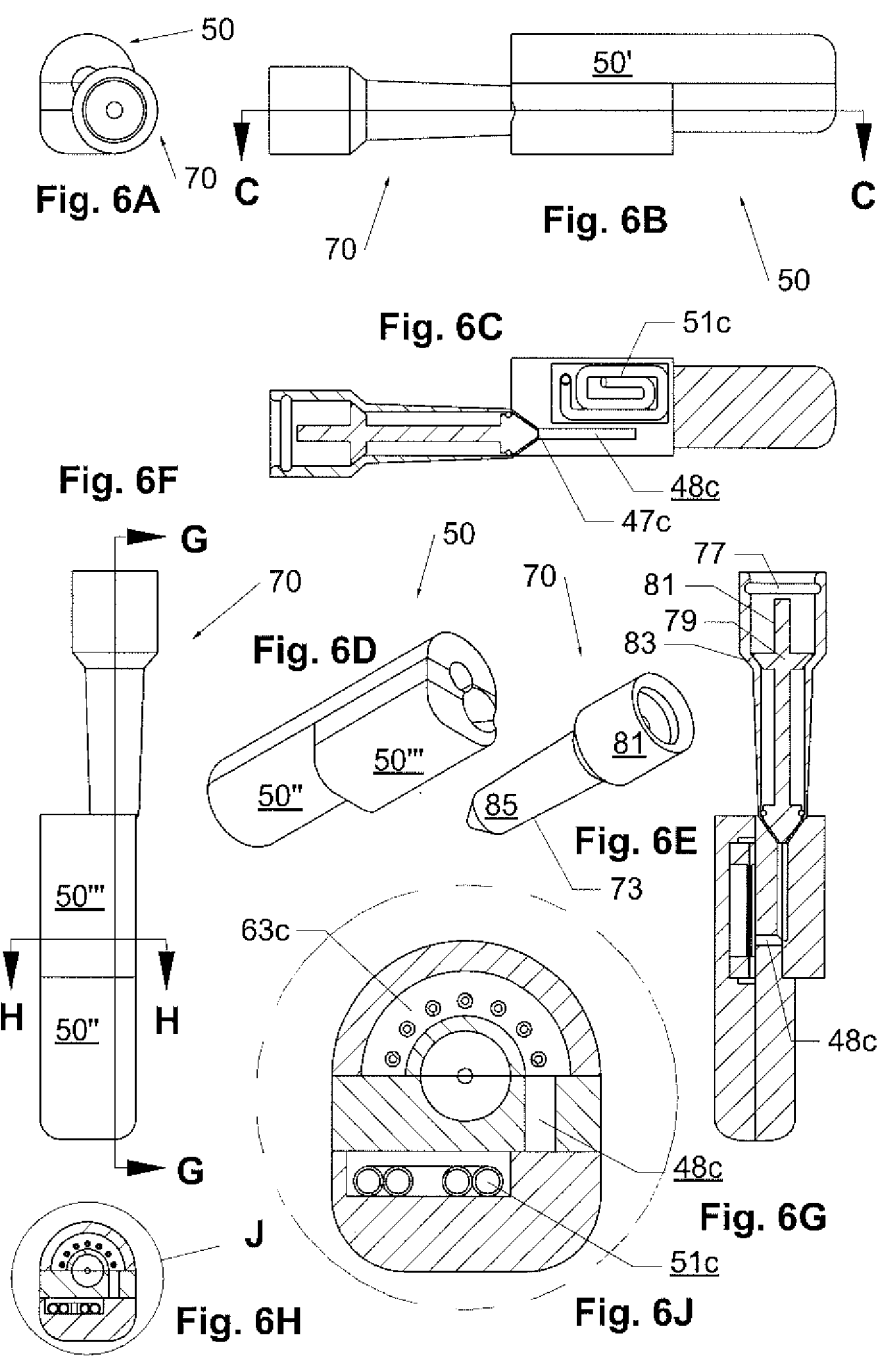

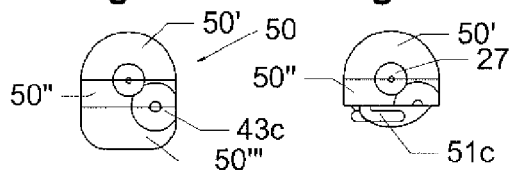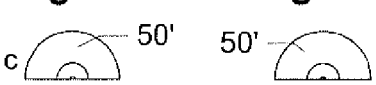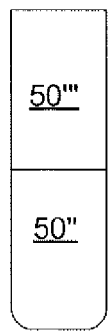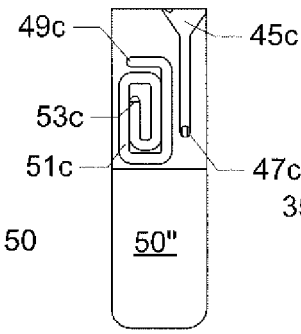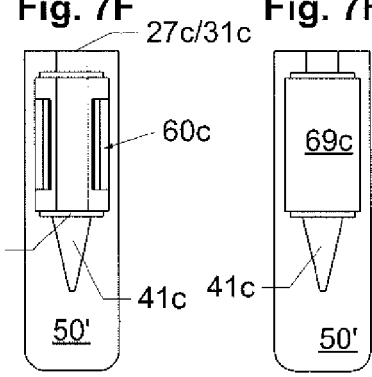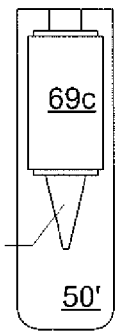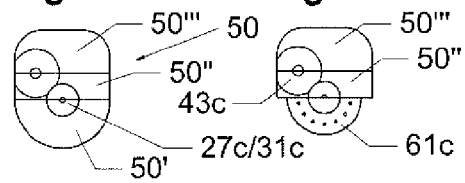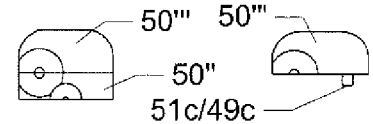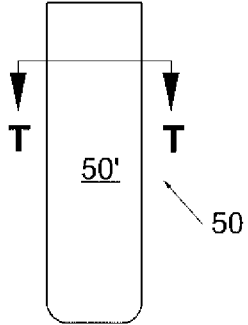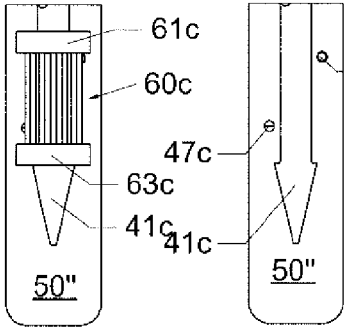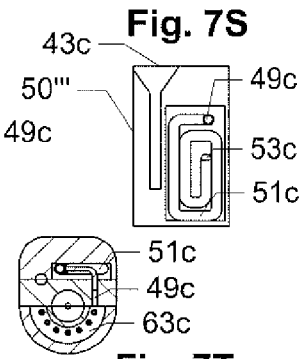

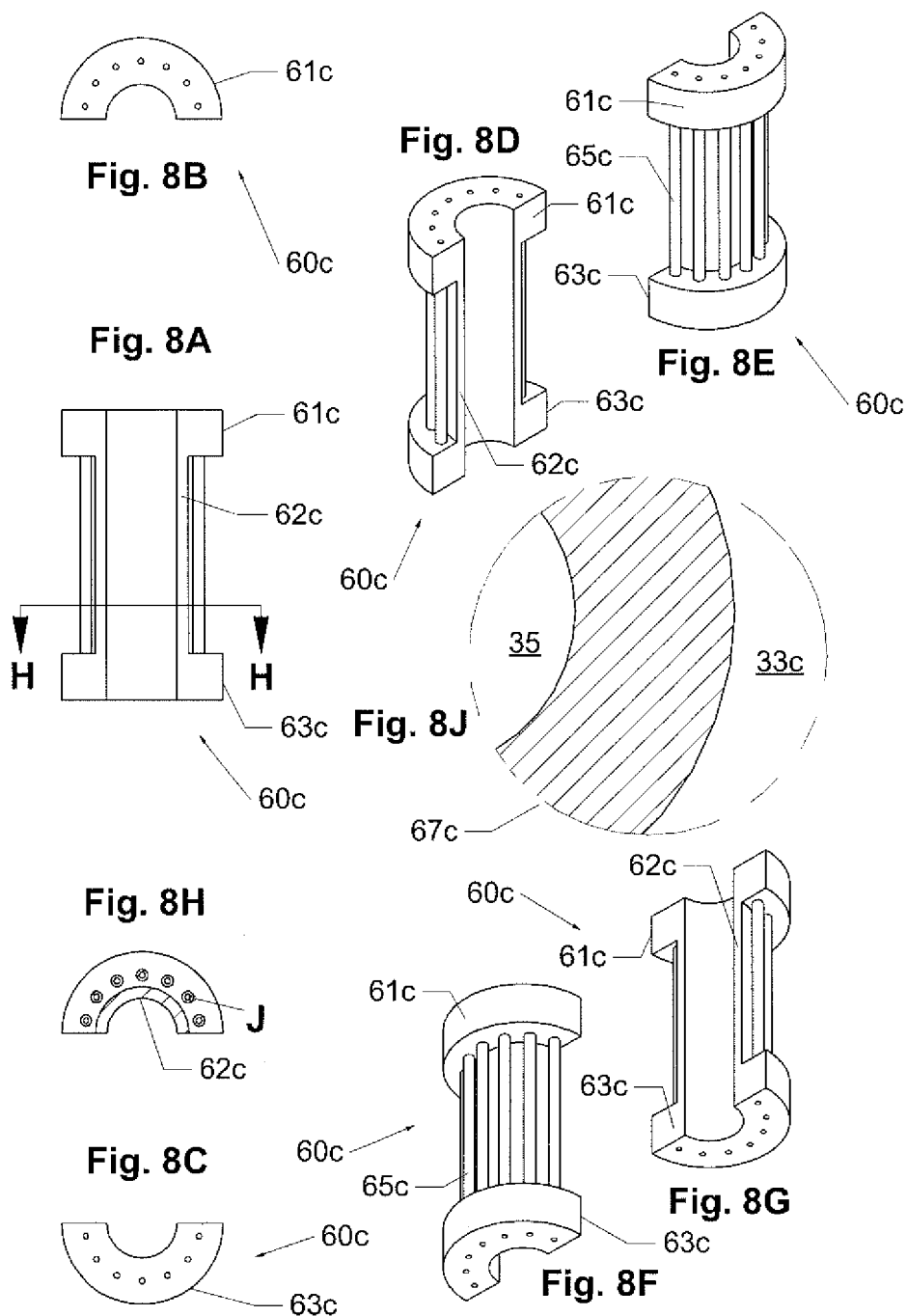

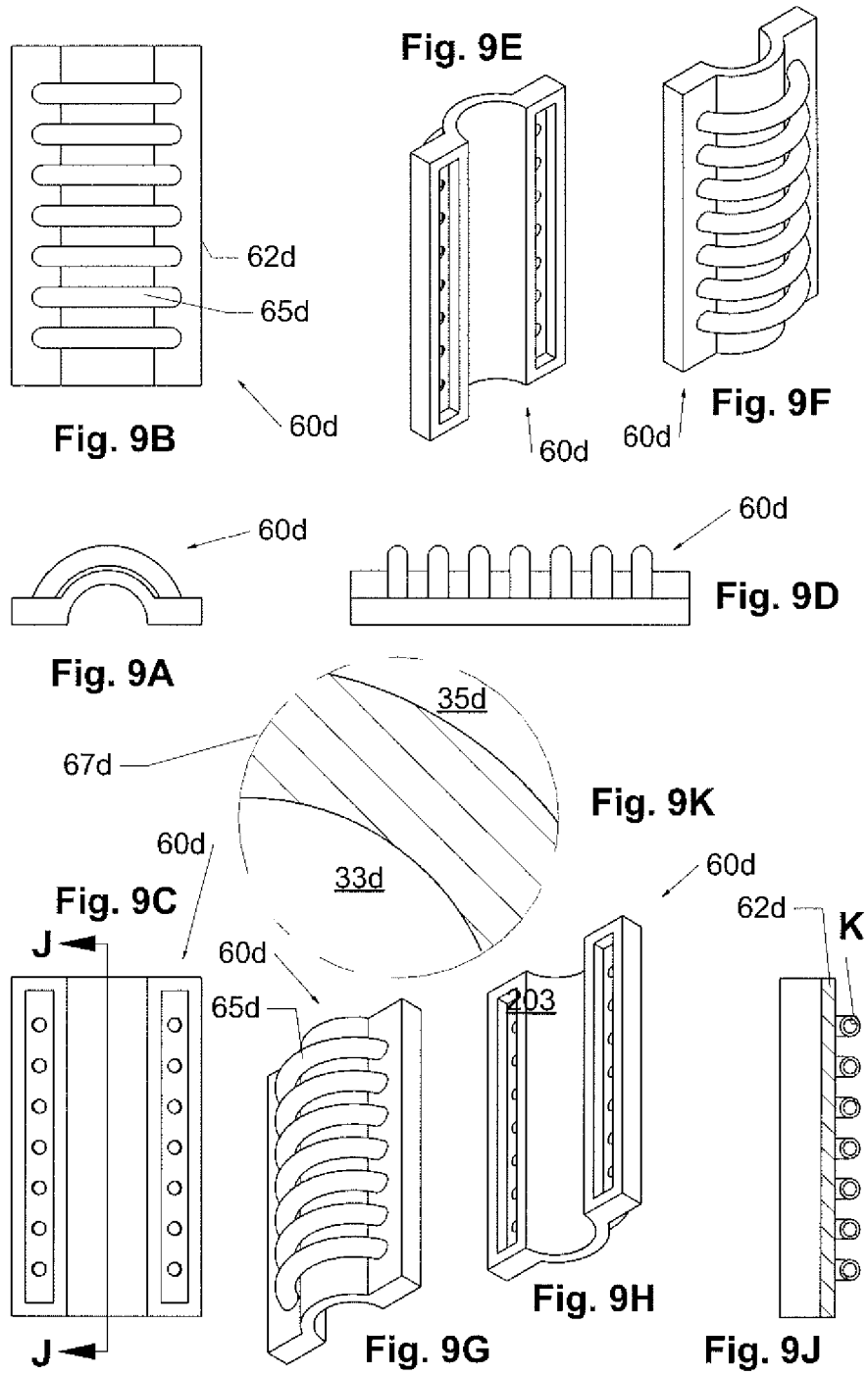

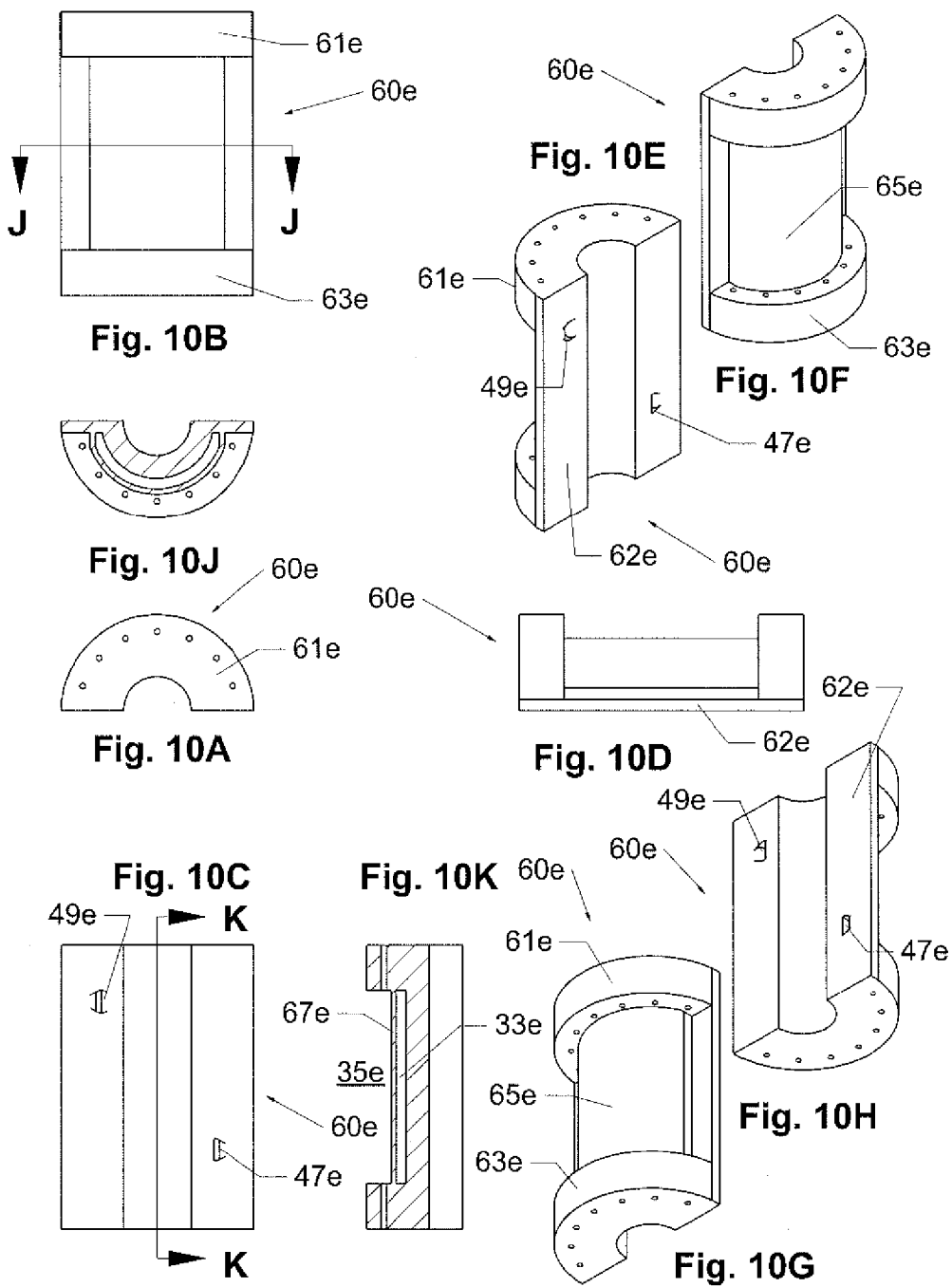

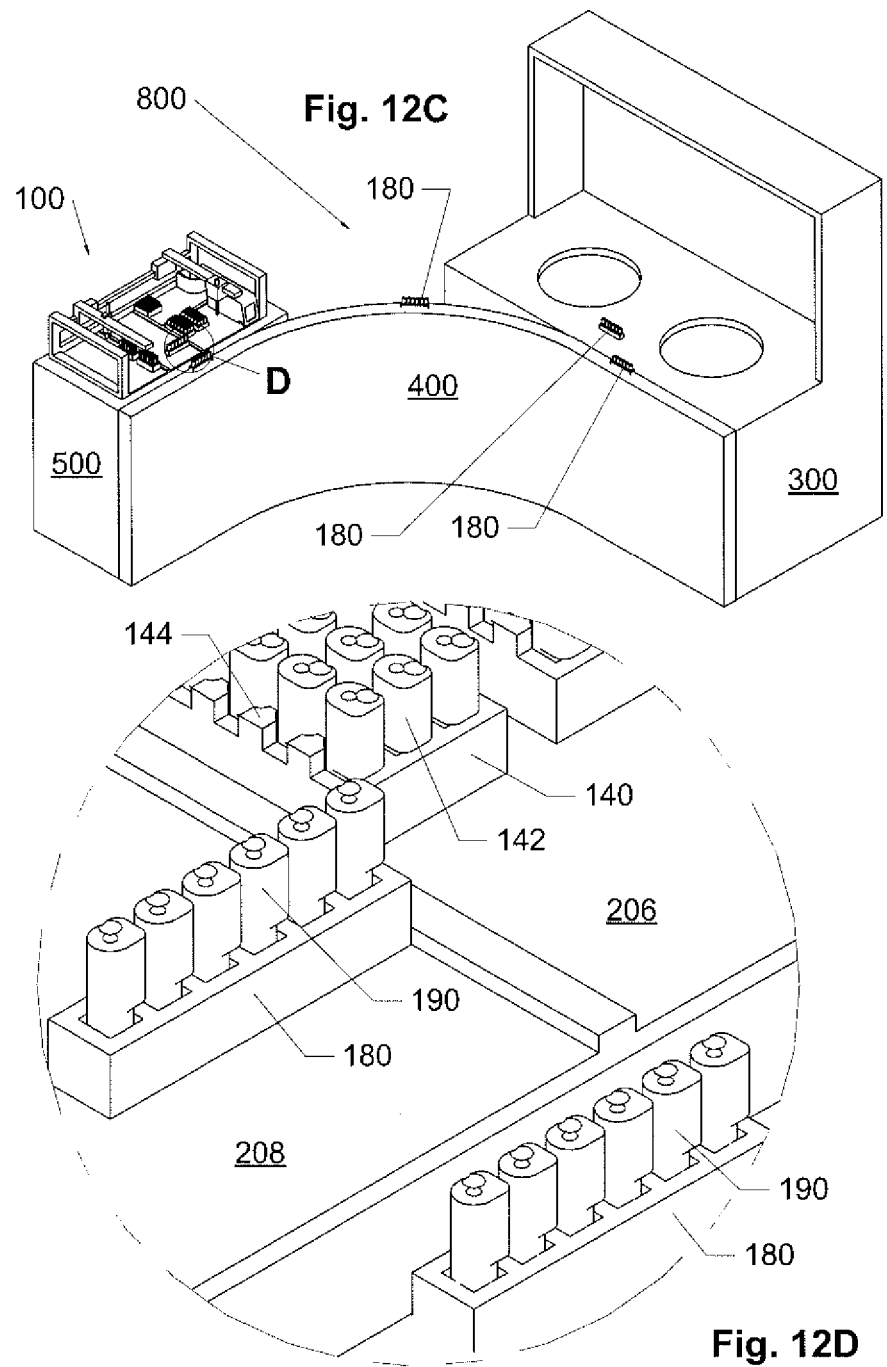

AUTOMATED ULTRA-FILTRATION APPARATUS

RELATED APPLICATIONS

This application is a continuation of PCT Patent Application No. PCT/CA2013/050935, filed Dec. 6, 2013, claiming the benefit of U.S. Provisional Patent Application No. 61/735,041, filed Dec. 9, 2012 entitled, "Disposable Ultra-filtration System", and is hereby incorporated by reference.

FIELD OF THE INVENTION

The invention relates to a disposable ultra-filtration cartridge for preparing an ultra-filtrate from a sample, for example serum and plasma samples, and laboratory automation incorporating the disposable ultra-filtration cartridge, whereby manual handling of samples, are minimized.

BACKGROUND OF THE INVENTION

Many medical diagnostic tests are performed in a medical laboratory, on serum and plasma. Serum is the yellow liquid obtained from whole blood after the blood is allowed to clot, and the clot is removed by centrifugation; plasma is the yellow liquid obtained from blood by centrifugation of blood mixed with an anticoagulant, e.g. heparin. Whole blood comprises the formed elements (i.e., the cellular components and the cell-derived components), and plasma. Red blood cells are the most abundant formed elements in blood, and platelets are examples of cell-derived components.

Measurement of the concentration of therapeutic drugs and certain hormones are essential in patient management, and usually, the total concentration of the drugs and hormones are measured because with the exception of a few hormones, e.g. thyroid hormones, the tests or assays are designed to measure the total concentrations. Designing an assay to measure the concentration of the free drugs/hormones are more complex. Only the free therapeutic drugs, ions and free hormones are available to cross vascular walls and biological membranes in order to produce biological activity, by attaching to specific and non-specific binding sites or receptors. Some examples of a therapeutic drug, an ion and a hormone are phenytoin, calcium and cortisol respectively.

Phenytoin, for example, is a therapeutic drug used to treat epilepsy. In the blood, about 90% of the phenytoin is bound to plasma proteins. Only the portion of phenytoin that is unbound or "free" is pharmacologically or biologically active. A test for total phenytoin represents the sum of the bound and unbound phenytoin. Under normal conditions, the balance between bound and unbound phenytoin in the blood is relatively stable, so measuring the total phenytoin is appropriate for monitoring therapeutic levels of phenytoin. However, in certain conditions and disease states, that balance can be upset, causing the percentage of free or active phenytoin to increase. Consequently, a patient may experience symptoms of phenytoin toxicity even though the total phenytoin concentration falls within a therapeutic range. In such cases, doctors may order serum or plasma free phenytoin in order to more reliably monitor the patient's phenytoin levels, instead of serum or plasma total phenytoin.

One method used to measure free phenytoin in a patient's serum or plasma sample involves: 1) adding the patient's sample to the sample reservoir of an ultra-filtration device; 2) capping the sample reservoir; 3) placing the ultra-filtration device in a centrifuge and centrifuging for about 25 minutes; and 4) measuring total phenytoin in the ultra-filtrate of the serum or plasma.

By way of examples only, some embodiments of a filtration apparatus that can be used to extract plasma from whole blood can be found in U.S. Pat. Nos. 7,816,124 and 7,807,450 awarded to the inventor. Subsequently, the inventor filed U.S. patent application Ser. No. 13/549,443 entitled "Sample Filtration Apparatus", which describe other embodiments of filtration assemblies.

In the case of a serum or plasma sample, the filtrate (or more appropriately, referred to as an ultra-filtrate since plasma is already considered to be a filtrate of whole blood) usually refers to the serum or plasma containing the smaller molecular weight substances like the free phenytoin, and the retentate usually refers to serum or plasma containing the higher molecular weight substances like the proteins that bind phenytoin. An example of such a protein is albumin, having a molecular weight of about 66 kilodaltons. In contrast, the molecular weight of phenytoin is about 0.25 kilodaltons. A person of ordinary skill in the art will appreciate that an ultra-filtrate is still a filtrate, and the term ultra-filtrate is used for clarity when the filtrate contains substances having low molecular weights relative to the molecular weight of large dissolved substances, for example large proteins like immunoglobulins. Also, it seems appropriate to call the fraction of plasma having the smaller molecular weight substances a plasma ultra-filtrate, since the starting sample is plasma, which is already considered to be a filtrate of blood.

U.S. patent application Ser. No. 13/549,443 filed by the inventor describes cartridges for extracting plasma and serum ultra-filtrate, but the devices can only be operated manually. Moreover, some embodiments of these devices require at least one manually operable compression chamber. Moreover, in operation the sample ultra-filtration chamber is not vented to the atmosphere. There is a need for an ultra-filtration cartridge that can be used in an automated laboratory system, where centrifugation is not required and manual handling of samples are minimal.

Laboratory automation is a strategy to develop, optimize and capitalize on technologies in the laboratory that enable new and improved processes for reducing laboratory process times. The most widely known application of laboratory automation technology is laboratory robotics. More generally, the field of laboratory automation comprises many different automated laboratory analyzers, devices, software algorithms, and methodologies used to enable, expedite and increase the efficiency and effectiveness of providing test results.

The automated process of providing plasma and serum ultra-filtrates, for example, can be incorporated in laboratory automation, and the plasma and serum ultra-filtrates used to measure therapeutic drugs, ions and hormones, for example.

SUMMARY OF THE INVENTION

The present invention provides a disposable ultra-filtration system for automatic preparation of an ultra-filtrate from a sample, the system comprising a disposable ultra-filtration cartridge and a disposable pipetting tip. The disposable ultra-filtration cartridge includes: a) a top end having at least one opening providing an ultra-filtrate chamber vent and an ultra-filtrate chamber opening; b) a bottom end for supporting the disposable ultra-filtration cartridge in an upright position in cooperation with a cartridge rack; c) a filtration chamber comprising (i) a membrane having a retentate side, a filtrate side, and a predetermined pore size, (ii) a sample inlet for sealably engaging the disposable pipetting tip containing the sample, (iii) a retentate outlet, (iv) an ultra-filtrate chamber defined substantially by the filtrate side of the membrane, an ultra-filtrate chamber opening for the ultra-filtrate to flow out of the ultra-filtrate chamber and the space therebetween, and (v) an ultra-filtrate chamber vent for enabling the ultra-filtrate to flow out of the ultra-filtrate chamber opening; d) a dead-end channel having an open end and a sealed end, wherein the open end is coincident with the retentate outlet; e) an ultra-filtrate reservoir at the bottom end for collecting the ultra-filtrate. The disposable pipetting tip includes a piston movable in one direction by applying a force to pressurize trapped air in the dead-end channel. When the force is relaxed the piston is movable in the opposite direction by the pressurized trapped air in the dead-end channel to accommodate reverse flow of retentate to unplug the pores.

The present invention also provides an automated workstation for preparing ultra-filtrate in a disposable ultra-filtration system, the automated workstation operating in cooperation with a controller and comprising: a) a base; b) one or more cartridge racks for holding the one or more disposable ultra-filtration cartridges of the disposable ultra-filtration system, and cartridge rack positions on the base for positioning the one or more cartridge racks in predetermined locations; c) cartridge rack detectors for detecting the presence of a cartridge rack on the base at the predetermined locations, the cartridge rack detectors having an output element for signaling the presence of the cartridge rack to the controller; d) one or more sample tube racks for holding one or more sample tubes, and sample tube rack positions on the base for positioning the sample tube racks in predetermined locations; e) sample tube rack detectors for detecting the presence of a sample tube rack on the base at the predetermined locations, the sample tube rack detectors having an output element for signaling the presence of the sample tube rack to the controller; f) one or more pipetting tip racks for holding one or more disposable pipetting tips of the disposable ultra-filtration system, and pipetting tip rack positions on the base for positioning the pipetting tip racks in predetermined locations; g) pipetting tip rack detectors for detecting the presence of a pipetting tip rack on the base at the predetermined locations, the pipetting tip rack detectors having an output element for signaling the presence of the pipetting tip rack to the controller; h) a pipetting tool for releasably engaging the one or more disposable pipetting tips; i) a movable arm, supported from the base, for supporting the pipetting tool; and j) a waste container for receiving released disposable pipetting tips. The pipetting tool is configured to apply a force to move a piston of the one or more disposable pipetting tips to pressurize trapped air in a dead-end channel of the one or more disposable ultra-filtration cartridges.

The present invention also provides a system for measuring at least one of a free therapeutic drug concentration and a free hormone concentration in one or more samples, the samples being one of serum and plasma, the system comprising: a) an analyzer calibrated to measure at least one of a total therapeutic drug concentration and a total hormone concentration; b) a controller comprising memory storage and a data input element for inputting processing instructions for the one or more samples, the processing instructions being stored in the memory storage; c) an automated workstation operating in cooperation with the controller, the automated workstation being capable of preparing one or more ultra-filtrates in one or more disposable ultra-filtration cartridges of a disposable ultra-filtration system, the automated workstation having a transport system for accepting the one or more samples and releasing the one or more ultra-filtrates in reservoirs of the one or more ultra-filtration cartridges, the automated workstation also having a pipetting tool for releasably engaging one or more disposable pipetting tips of the disposable ultra-filtration system; and d) a track for transporting the one or more ultra-filtrates from the automated workstation to the analyzer. The analyzer is used to measure at least one of a free therapeutic drug concentration and a free hormone concentration in the one or more ultra-filtrates prepared by the automated workstation. The pipetting tool is configured to apply a force to move a piston of the one or more disposable pipetting tips to pressurize trapped air in a dead-end channel of the one or more disposable ultra-filtration cartridges.

Some embodiments of the system further comprise an indicia reader for tracking the one or more sample tubes and the one or more disposable ultra-filtration cartridges. The indicia comprises one of a one-dimensional barcode, a two-dimensional barcode, and a radio frequency identification tag attached to the one or more sample tubes and the one or more disposable ultra-filtration cartridges.

Other aspects and features of the present invention will become apparent, to those ordinarily skilled in the art, upon review of the following description of the specific embodiments of the invention.

BRIEF DESCRIPTION OF THE DRAWINGS

For a better understanding of the present invention, and to show more clearly how it may be carried into effect, reference will now be made, by way of example, to the accompanying drawings, which illustrate aspects of embodiments of the present invention and in which:

FIG. 1A is a schematic drawing showing details of a top view of an ultra-filtration cartridge 20 used for preparing an ultra-filtrate according to a first embodiment of the ultra-filtration cartridge;

FIG. 1B is a right side view of the cartridge 20 shown in FIG. 1A;

FIG. 10 is a first cross-sectional view through the cartridge 20 shown in FIG. 1B along line C-C;

FIG. 1D is a front view of the cartridge 20 shown in FIG. 1A;

FIG. 1E is a second cross-sectional view through the cartridge 20 shown in FIG. 1D along line E-E;

FIG. 1F is a third cross-sectional view through the cartridge 20 shown in FIG. 1D along line F-F;

FIG. 1G is a perspective view of the apparatus 20 shown in FIG. 1A;

FIG. 2F is a detailed view of detail F shown in FIG. 2E showing a schematic representation of the membrane 67a;

FIG. 3A is a schematic drawing showing details of a top view of an assembly comprising an ultra-filtration cartridge 40 according to a second embodiment of the ultra-filtration cartridge, sealably engaged with a pipetting tip 70, used for preparing an ultra-filtrate;

FIG. 3B is a front view of the assembly comprising the cartridge 40 and the pipetting tip 70 shown in FIG. 3A;

FIG. 3C is a first cross-sectional view through the assembly comprising the cartridge 40 and the pipetting tip 70 shown in FIG. 3B along line C-C;

FIG. 3D is a second cross-sectional view through the assembly comprising the cartridge 40 and the pipetting tip 70 shown in FIG. 3B along line D-D;

FIG. 3E is a perspective view of the pipetting piston 87 shown in cross-section in FIG. 3D;

FIG. 3F is a perspective view of the pipetting tip 70 alone;

FIG. 3G is a perspective view of the upper portion 30 of the cartridge 40 shown FIG. 3A, FIG. 3B and FIG. 3D;

FIG. 3H is a perspective view of the lower portion 10 of the cartridge 40 shown FIG. 3A, FIG. 3B and FIG. 3D;

FIG. 4A is a schematic drawing showing details of a top view of the ultra-filtration cartridge 40 used for preparing an ultra-filtrate according to the second embodiment of the ultra-filtration cartridge, comprising the upper section 30 shown in two parts 30' and 30", and the lower section 10, with section 30" at the top;

FIG. 4B is a front view of the cartridge 40 shown in FIG. 4A;

FIG. 4C is a top view of cartridge 40 shown in FIG. 4A, with parts 30" and lower section 10 hidden;

FIG. 4D is a front view of the cartridge 40 shown in FIG. 4C,

FIG. 4E is a top view of cartridge 40 shown in FIG. 4A, with parts 30", lower section 10 and filtration membrane assembly 60b hidden;

FIG. 4F is a front view of the cartridge 40 shown in FIG. 4E;

FIG. 4G is a schematic drawing showing details of a top view of an ultra-filtration cartridge 40 used for preparing an ultra-filtrate according to a second embodiment of the ultra-filtration cartridge, comprising the upper section 30 shown in two parts 30' and 30", and the lower section 10, with section 30' at the top;

FIG. 4H is a front view of the cartridge 40 shown in FIG. 4G;

FIG. 4J is a top view of cartridge 40 shown in FIG. 4G, with parts 30' and lower section 10 hidden;

FIG. 4K is a front view of the cartridge 40 shown in FIG. 4J;

FIG. 4L is a top view of cartridge 40 shown in FIG. 4G, with parts 30', lower section 10 and filtration membrane assembly 60b hidden;

FIG. 4M is a front view of the cartridge 40 shown in FIG. 4L;

FIG. 5A is a schematic drawing showing details of a front view of the filtration membrane assembly 60b shown in FIG. 4D and FIG. 4K;

FIG. 5B is a top view of the filtration membrane assembly 60b shown in FIG. 5A;

FIG. 5C is a bottom view of the filtration membrane assembly 60b shown in FIG. 5A;

FIG. 5D is a first perspective view of the filtration membrane assembly 60b shown in FIG. 5A;

FIG. 5E is a second perspective view of the filtration membrane assembly 60b shown in FIG. 5A;

FIG. 5F is a third perspective view of the filtration membrane assembly 60b shown in FIG. 5A;

FIG. 5G is a fourth perspective view of the filtration membrane assembly 60b shown in FIG. 5A;

FIG. 5H is a cross-sectional view of the filtration membrane assembly 60b shown in FIG. 5A along line H-H;

FIG. 5J is a detailed view of detail J shown in FIG. 5H showing a schematic representation of the membrane 67b;

FIG. 6A is a schematic drawing showing details of a top view of an assembly comprising an ultra-filtration cartridge 50 according to a third embodiment of the ultra-filtration cartridge, engaged with a pipetting tip 70, used for preparing an ultra-filtrate;

FIG. 6B is a right side view of the assembly comprising the cartridge 50 and the pipetting tip 70 shown in FIG. 6A;

FIG. 6C is a first cross-sectional view through the assembly comprising the cartridge 50 and the pipetting tip 70 shown in FIG. 6B along line C-C;

FIG. 6D is a perspective view of the cartridge 50 shown FIG. 6B and FIG. 6F;

FIG. 6E is a perspective view of the pipetting tip 70 shown FIG. 6B and FIG. 6F;

FIG. 6F is a front view of the assembly comprising the cartridge 50 and the pipetting tip 70 shown in FIG. 6A;

FIG. 6G is a second cross-sectional view through the assembly comprising the cartridge 50 and the pipetting tip 70 shown in FIG. 6F along line G-G;

FIG. 6H is a third cross-sectional view through the assembly comprising the cartridge 50 and the pipetting tip 70 shown in FIG. 6F along line H-H;

FIG. 6J is an enlarged of the cross-sectional view shown in FIG. 6H;

FIG. 7A is a schematic drawing showing details of a top view of an ultra-filtration cartridge 50 used for preparing an ultra-filtrate according to a third embodiment of the ultra-filtration cartridge, shown in three parts 50', 50" and 50"', with the part 50"' at the bottom;

FIG. 7B is a front view of the cartridge 50 shown in FIG. 7A;

FIG. 7C is a top view of cartridge 50 shown in FIG. 7A, with front part 50"' hidden;

FIG. 7D is a front view of the cartridge 50 shown in FIG. 7C,

FIG. 7E is a top view of cartridge 50 shown in FIG. 7A, with the front part 50"' and the middle part 50" hidden;

FIG. 7F is a front view of the cartridge 50 shown in FIG. 7E;

FIG. 7G is a top view of the cartridge 50 shown in FIG. 7A, with the front part 50"', the middle part 50" and the and filtration membrane assembly 60c hidden;

FIG. 7H is a front view of the cartridge 50 shown in FIG. 7G;

FIG. 7J is a schematic drawing showing details of a top view of an ultra-filtration cartridge 50 used for preparing an ultra-filtrate according to a third embodiment of the ultra-filtration cartridge, shown in three parts 50', 50" and 50"', with the part 50' at the bottom;

FIG. 7K is a front view of the cartridge 50 shown in FIG. 7J;

FIG. 7L is a top view of cartridge 50 shown in FIG. 7J, with back part 50' hidden;

FIG. 7M is a front view of the cartridge 50 shown in FIG. 7L;

FIG. 7N is a top view of cartridge 50 shown in FIG. 7J, with the back part 50' and the filtration membrane assembly 60c hidden;

FIG. 7P is a front view of the cartridge 50 shown in FIG. 7N;

FIG. 7R is a top view of the cartridge 50 shown in FIG. 7A, with the back part 50', the filtration membrane assembly 60c and the middle part 50" hidden;

FIG. 7S is a front view of the cartridge 50 shown in FIG. 7R;

FIG. 7T is a cross-sectional view through the cartridge 50 shown in FIG. 7K along line T-T;

FIG. 8A is a schematic drawing showing details of a front view of the filtration membrane assembly 60c shown in FIG. 6F and FIG. 6M;

FIG. 8B is a top view of the filtration membrane assembly 60c shown in FIG. 8A;

FIG. 8C is a bottom view of the filtration membrane assembly 60c shown in FIG. 8A;

FIG. 8D is a first perspective view of the filtration membrane assembly 60c shown in FIG. 8A;

FIG. 8E is a second perspective view of the filtration membrane assembly 60c shown in FIG. 8A;

FIG. 8F is a third perspective view of the filtration membrane assembly 60c shown in FIG. 8A;

FIG. 8G is a fourth perspective view of the filtration membrane assembly 60c shown in FIG. 8A;

FIG. 8H is a cross-sectional view of the filtration membrane assembly 60c shown in FIG. 8A along line H-H;

FIG. 8J is a detailed view of detail J shown in FIG. 8H showing a schematic representation of the membrane 67c;

FIG. 9A is a schematic drawing showing details of a top view of another embodiment 60d of a filtration membrane assembly;

FIG. 9B is a back view of the filtration membrane assembly 60d shown in FIG. 9A;

FIG. 9C is a front view of the filtration membrane assembly 60d shown in FIG. 9A;

FIG. 9D is a right side view of the filtration membrane assembly 60d shown in FIG. 9A;

FIG. 9E is a first perspective view of the filtration membrane assembly 60d shown in FIG. 9A;

FIG. 9F is a second perspective view of the filtration membrane assembly 60d shown in FIG. 9A;

FIG. 9G is a third perspective view of the filtration membrane assembly 60d shown in FIG. 9A;

FIG. 9H is a fourth perspective view of the filtration membrane assembly 60d shown in FIG. 9A;

FIG. 9J is a cross-sectional view of the filtration membrane assembly 60d shown in FIG. 9C along line J-J;

FIG. 9K is a detailed view of detail K shown in FIG. 9J showing a schematic representation of the membrane 67d;

FIG. 10A is a schematic drawing showing details of a top view of another embodiment 60e of a filtration membrane assembly;

FIG. 10B is a back view of the filtration membrane assembly 60e shown in FIG. 9A;

FIG. 10O is a front view of the filtration membrane assembly 60e shown in FIG. 10A;

FIG. 10D is a right side view of the filtration membrane assembly 60e shown in FIG. 10A;

FIG. 10E is a first perspective view of the filtration membrane assembly 60e shown in FIG. 10A;

FIG. 10F is a second perspective view of the filtration membrane assembly 60e shown in FIG. 10A;

FIG. 10G is a third perspective view of the filtration membrane assembly 60e shown in FIG. 10A, FIG. 10H is a fourth perspective view of the filtration membrane assembly 60e shown in FIG. 10A, FIG. 10J is a first cross-sectional view of the filtration membrane assembly 60e shown in FIG. 10B along line J-J;

FIG. 10K is a second cross-sectional view of the filtration membrane assembly 60e shown in FIG. 100 along line K-K;

FIG. 11D is a first perspective view of the workstation 100 shown in FIG. 11A,

FIG. 12C is perspective view of the system 800 shown in FIG. 12A; and

FIG. 12D is a detailed view of detail D shown in FIG. 12C showing details of ultra-filtration cartridges in an ultra-filtration cartridge rack, ultra-filtration cartridge reservoir containing sample ultra-filtrate, in an analyzer sector for presenting sample ultra-filtrate to the analyzer, and ultra-filtration cartridge reservoir containing sample ultra-filtrate in an analyzer sector, on a transport track used to present the sample ultra-filtrate to the analyzer.

DETAILED DESCRIPTION OF PREFERRED EMBODIMENTS

Figure 2A:
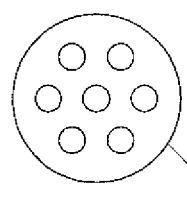
FIG. 2A is schematic drawing showing details of a top view of a hollow fiber filtration membrane assembly 60a shown in FIGS. 10 and 1F.
Figure 2B:
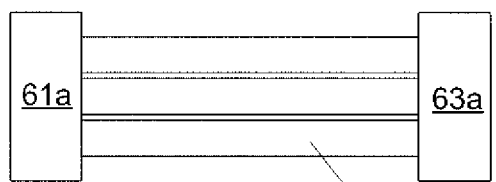
FIG. 2B is a right side view of the hollow fiber filtration membrane assembly 60a shown in FIGS. 10 and 1F.
Figure 2C:
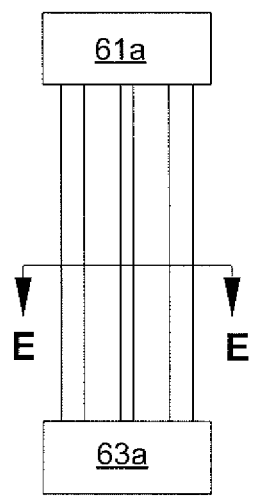
FIG. 2C is a front view of hollow fiber filtration membrane assembly 60a shown in FIG. 2A.
Figure 2D:
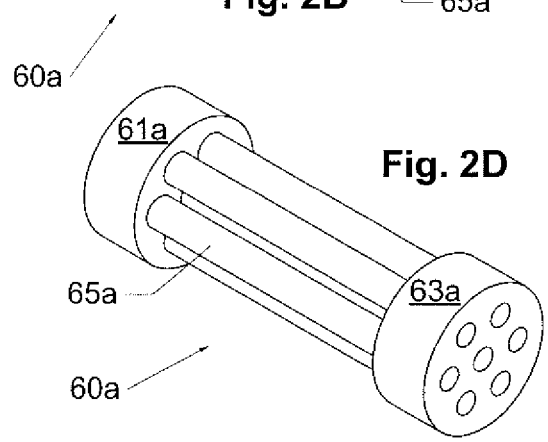
FIG. 2D is a perspective view of the hollow fiber filtration membrane assembly 60a shown in FIG. 2A
Figure 2E:
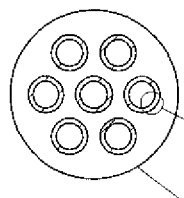
FIG. 2E is a cross-sectional view through the hollow fiber filtration membrane assembly 60a shown in FIG. 2C along line E-E.

The reference numerals used in describing the preferred embodiments of the invention are provided in Table 1.

TABLE 1

| Reference Numerals | Description of Structural Features |
|---|---|
| 10 | A body of an ultra-filtration cartridge reservoir according to the second embodiment of an ultra-filtration cartridge |
| 20 | A first embodiment of an ultra-filtration cartridge |
| 27 | An opening for allowing access to ultra-filtrate reservoir |
| 30 | A body comprising a filtration chamber of an ultra-filtration cartridge according to the second embodiment of an ultra-filtration cartridge |
| 31 | A vent fluidly connected to the filtrate side of the membrane |
| 33 | Retentate side of membrane and adjacent space |
| 35 | Filtrate side of membrane and adjacent space, the adjacent space being a portion of an ultra-filtrate chamber (An ultra-filtration chamber is not shown as a specific structure, but refers substantially to space defined by the filtrate side of the membrane, the ultra-filtrate chamber outlet 39, and the space therebetween) |
| 37 | A channel fluidly connecting filtrate side of membrane and adjacent space, with ultra-filtrate chamber outlet |
| 39 | An ultra-filtrate chamber outlet |
| 40 | A second embodiment of an ultra-filtration cartridge |
| 41 | A bottom cavity of an ultra-filtrate reservoir of an ultra-filtration cartridge |
| 43 | An opening for allowing pipetting tip to access inlet of the filtration chamber |
| 45 | A cavity occupied by a pipetting tip when the pipetting tip is engaged with ultra-filtration cartridge |

TABLE 1-continued

| Reference Numerals | Description of Structural Features |
|---|---|
| 47 | A filtration chamber inlet for sealably engaging pipetting tip |
| 48 | An extension of the filtration inlet, fluidly connected to the filtration chamber |
| 49 | A filtration chamber outlet, coincident with the open end of a dead-end channel 51 |
| 50 | A third embodiment of an ultra-filtration cartridge |
| 51 | A dead-end channel of an ultra-filtration cartridge |
| 53 | A sealed end of a dead-end channel 51 of an ultra-filtration cartridge |
| 60 | A filtration membrane assembly |
| 61 | A first flange in membrane assembly |
| 62 | A filtration membrane assembly supporting structure |
| 63 | A second flange in membrane assembly |
| 65 | A hollow fiber filtration membrane |
| 67 | A filtration membrane (Wall of a hollow fiber filter when the filtration membrane is in the form of a hollow fiber filter) |
| 69 | A cavity usually occupied by a filtration membrane assembly |
| 70 | A pipetting tip |
| 73 | A pipetting tip housing |
| 77 | A pipetting tip housing recess |
| 79 | A pipetting tip piston flange |
| 81 | A pipetting tip housing gripping end |
| 83 | A pipetting tip housing piston flange stop (inclined interior wall of pipetting tip housing) |
| 85 | A pipetting tip dispensing end |
| 87 | A pipetting tip piston |
| 89 | A pipetting tip piston gripping stem |
| 91 | A pipetting tip piston flange upper face |
| 93 | A pipetting tip piston flange lower face |
| 95 | A pipetting tip piston sealing O-ring |
| 100 | A workstation for automatically preparing sample ultra-filtrate from the sample |
| 110 | Pipetting tool for releasably holding a pipetting tip |
| 112 | A pipetting tool carriage for supporting and cooperating with pipetting tool |
| 114 | A pipetting tool carriage movable arm for supporting and moving pipetting tool carriage |
| 116 | A pipetting tool carriage movable arm carriage |
| 120 | A pipetting tip rack |
| 122 | A pipetting tip |
| 130 | A gripping tool for gripping for example, a sample tube or an ultra-filtration cartridge, to enable transportation thereof |
| 132 | A gripping tool carriage for supporting and cooperating with gripping tool |
| 134 | A gripping tool carriage movable arm for supporting and moving gripping tool carriage |
| 136 | A gripping tool carriage movable arm |
| 138 | A track for facilitating movement of pipetting tool carriage movable arm carriage and gripping tool carriage movable arm |
| 140 | An ultra-filtration cartridge rack |
| 142 | An ultra-filtration cartridge (one similar to the third embodiment of an ultra-filtration cartridge 50 is shown) |
| 144 | A projected member in the ultra-filtration cartridge rack, for enabling proper orientation of ultra-filtration cartridge when it is located in the ultra-filtration rack for processing a sample |
| 150 | A sample tube rack |
| 152 | A sample tube |
| 160 | A waste container for receiving ejected used pipetting tip |
| 170 | A controller |
| 172 | A controller data input element and display touch screen |
| 180 | An analyzer sector for presenting sample ultra-filtrate to the analyzer |
| 190 | An ultra-filtration cartridge reservoir containing sample ultra-filtrate (The third embodiment of an ultra-filtration cartridge is shown as this example, wherein the reservoir is an integral part of the ultra-filtration cartridge.) |
| 200 | An automated workstation base |
| 202 | An automated workstation supporting frame |
| | A pipetting tip rack site for housing pipetting tips contained in pipetting tip racks |
| 204 | A sample delivery site on the workstation for receiving samples in sample tubes contained in sample tube racks |
| 206 | An ultra-filtration cartridge rack site for on the workstation for housing ultra-filtration cartridges contained in ultra-filtration cartridge racks |

TABLE 1-continued

| Reference Numerals | Description of Structural Features |
|---|---|
| 208 | An analyzer sector site on the workstation for housing analyzer sectors |
| 300 | An analyzer, for example, an immunoanalyzer for performing immunoassays |
| 400 | A transport track for transporting a single ultra-filtration cartridge reservoir containing sample ultra-filtrate or a plurality of ultra-filtration cartridge reservoirs containing sample ultra-filtrates in analyzer sectors |
| 500 | A workstation table for aligning the workstation with the analyzer on a horizontal plane |
| 800 | An ultra-filtration system for measuring free therapeutic drugs and free hormones in serum or plasma |

The same reference numerals are used to represent similar structural features in different embodiments. In some cases, letters are added to the end of the numerals to indicate different embodiments. For example, the indicia 60 is used to represent a filtration membrane assembly, but in the first embodiment (20), second embodiment (40), and third embodiment (50), the indicia 60a, 60b, and 60c are used to refer to the filtration membrane assembly in the respective embodiments.

The present invention describes several embodiments of disposable ultra-filtration cartridges for automatic preparation of sample ultra-filtrates. The sample used with the present invention is one of serum or plasma. However, the sample can be any biological sample as well as a non-biological sample. The ultra-filtration cartridge can be used in a stand-alone automated workstation operating in cooperation with a controller, or can be used in an automated workstation that is integrated into an automated laboratory, operating in cooperation with a more centralized controller.

To the best knowledge of the inventor, there is no known automated workstation or system that includes ultra-filtration cartridges for preparing sample ultra-filtrates automatically, without the use of a centrifuge. Moreover, there is no known automated system for measuring free fractions (i.e., not bound to substantially larger molecules like proteins, for example albumin) of a therapeutic drug or a hormone, using the assays designed to measure total drug or total hormone concentration in plasma or serum.

Disposable ultra-filtration cartridges are described, followed by an automated workstation, and finally a system that expands beyond the workstation is described. Some embodiments of the ultra-filtration cartridges are described as seamless units and some are described as comprising parts that can be easily manufactured by for example, plastic molding or 3-D printing; the parts are then assembled together using for example, double-sided sticky gasket, application of glue to the faces or ultrasonic welding. By illustrating some of the embodiments of cartridges in parts, ideas are provide regarding manufacturing the cartridges, and the parts provide views of internal structures, without having to view cross-sections.

An element of the disposable ultra-filtration cartridges is a filtration membrane assembly. Several embodiments of filtration membrane assembly are illustrated, for example filtration membrane assemblies 60a illustrated in FIGS. 2A-2F, 60b illustrated in FIGS. 5A-5J, 60c illustrated in FIGS. 8A-8J, 60d illustrated in FIGS. 9A-9K, and 60e illustrated in FIGS. 10A-10K. For a more general description of a membrane, the side of the membrane in contact with retentate is referred to as the retentate side, and the side of the membrane in contact with the filtrate is referred to as the filtrate side. When the sample is plasma, the retentate will initially be plasma, which progressively becomes more concentrated plasma; the filtrate will be a plasma ultra-filtrate. A person of ordinary skill in the art will appreciate that the membrane could take on any shape, provided that the membrane allows sample ultra-filtrate to travel from the retentate side to the filtrate side, and a barrier is maintained between the retentate side and the filtrate side. The pore size of the membrane depends on the size of molecules that are required to pass through the filtration membrane.

Another element of the present invention is a filtration chamber. A person of ordinary skill in the art will appreciate that a filtration chamber does not point to any isolated structure in the embodiments of the invention, but refers to a general structure that comprises a filtration membrane assembly, a sample inlet fluidly connected to the retentate side of the membrane, and a retentate outlet for outflow of the fraction of sample that does not penetrate the membrane, and an outlet for the fraction of sample that penetrates the membrane. The space occupied by the filtration chamber is illustrated as cavity 69a in FIG. 1E. Flow across a surface of the membrane effectively reduces sample viscosity, and unplugs the membrane pores.

Referring collectively to FIGS. 1A-1G, shown are different views of an ultra-filtration cartridge 20 according to a first embodiment of an ultra-filtration cartridge. Cartridge 20 represents a disposable ultra-filtration cartridge for automatic preparation of sample ultra-filtrate. The cartridge has a top end shown in FIG. 1A, and a bottom end for supporting the cartridge in an upright position in cooperation with a cartridge rack. The cartridge can be provided in individual holders or racks for holding more than one cartridge. The bottom end is shown in FIG. 1D as the part towards the bottom of the page, and in FIG. 1B as the part towards the right side of the page. At the top end is shown an opening 27a for allowing access to an ultra-filtrate reservoir 41a, a vent 31a for enabling the ultra-filtrate to flow into the ultra-filtrate reservoir 41a, and an opening 43 for allowing a pipetting tip to access sample inlet 47a of a filtration chamber. Also shown in FIG. 1A is an ultra-filtrate chamber outlet 39a, shown clearly in FIG. 1C. A right side view, a top view and a perspective view of ultra-filtration cartridge 20 are shown in FIGS. 1B, 1D, and 1G respectively. The bottom of the cartridge is intended to fit in a cartridge rack or analyzer sector, so that the opening 27a to the ultra-filtrate reservoir 41a is substantially concentric with the annular shape of the bottom of the cartridge, in order for an analyzer sampling probe to have unobstructive access to the ultra-filtrate.

A cross-sectional view of the cartridge 20 shown in FIG. 1B through line C-C is shown as FIG. 10. Shown are a filtration membrane assembly 60a, portion of the an ultra-filtrate chamber shown as 35a, the ultra-filtrate chamber outlet 39a, and a vent 31a fluidly connected to the ultra-filtrate chamber, and a channel 37a fluidly connecting filtrate side of membrane and adjacent space 35a with the ultra-filtrate chamber outlet 39a. The ultra-filtrate chamber is not shown as a specific structure, but refers substantially to space defined by the filtrate side of the membrane, the ultra-filtrate chamber outlet 39a, and the space therebetween. Also shown is a cross-sectional view of a dead-end channel 51a (see FIG. 1E).

Figure 2F:
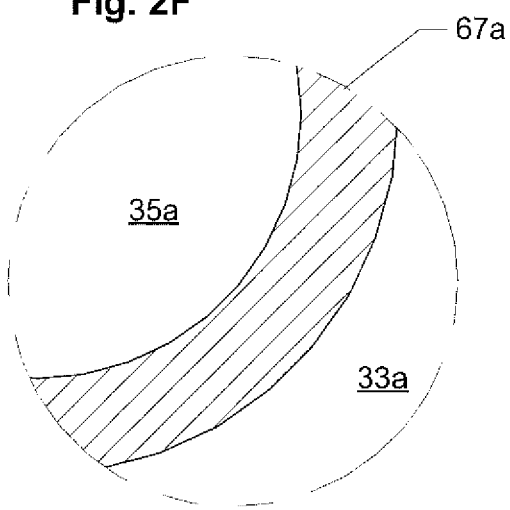

Cross-sectional views of the cartridge 20 shown in FIG. 1D through lines E-E and F-F are shown as FIGS. 1E and 1F respectively. A cavity 69a is shown in FIG. 1E, which is usually occupied by the membrane assembly 60a, and is therefore a substantial representation the space occupied by the filtration chamber. Details of the filtration membrane assembly 60a are shown collectively in FIGS. 2A-2F. The filtration membrane assembly 60a comprises hollow fibers 65a, and perforated flanges 61a and 63a. The flanges 61a and 63a provide support for the individual hollow fibers 65a, and the annular surface of the flanges provide seals when the assembly 60a is installed in the cavity 69a. The outside portions of the fibers 65a are also sealed at the flanges, in order to provide fluid-tight separation between ultra-filtrate and retentate. Sealing can be accomplished by, for example, a resin or glue, without obstructing the lumens of the fibers. A cross-section of the membrane 67a, which is the wall of the hollow fiber, is shown as F in FIG. 2E, and details of F is shown in FIG. 2F, showing the filtrate side 35a, and the retentate side 33a of the membrane 67a. In other embodiments as illustrated in FIG. 9K for example, the filtrate side is 33d and the retentate side is 35d.

Referring to FIG. 1E, shown is a dead-end channel 51a having an open end 49a and a sealed end 53a. The open end 49a of the dead-end channel 51a is coincident with the filtration chamber outlet. Also shown is a cavity 45a occupied by a pipetting tip when the pipetting tip is engaged with ultra-filtration cartridge. Details of a pipetting tip 70 are shown in FIGS. 3B, 3D, and 3F, in association with a second embodiment 40 of an ultra-filtration cartridge. In operation the sample inlet 47a is sealably engaged with the dispensing end 85 of a disposable pipetting tip 70 containing sample.

Referring to FIGS. 3B, 3D, 3E, and 3F, shown are details of the pipetting tip 70. The pipetting tip 70 comprises a pipetting tip housing 73, a pipetting tip housing recess 77, a pipetting tip piston flange 79, a pipetting tip housing gripping end 81, a pipetting tip housing piston flange stop (inclined interior wall of pipetting tip housing) 83, a pipetting tip dispensing end 85, a pipetting tip piston 87, a pipetting tip piston gripping stem 89, a pipetting tip piston flange upper face 91, a pipetting tip piston flange lower face 93, and a pipetting tip piston sealing O-ring 95 at a piston sealing end (or any other means for moving the piston 87 inside the pipetting tip housing 73 in a fluid-tight manner). This type of positive displacement pipetting system is known, for example, U.S. Pat. No. 4,474,071 teaches a manually operable positive displacement pipette.

Figure 11A:
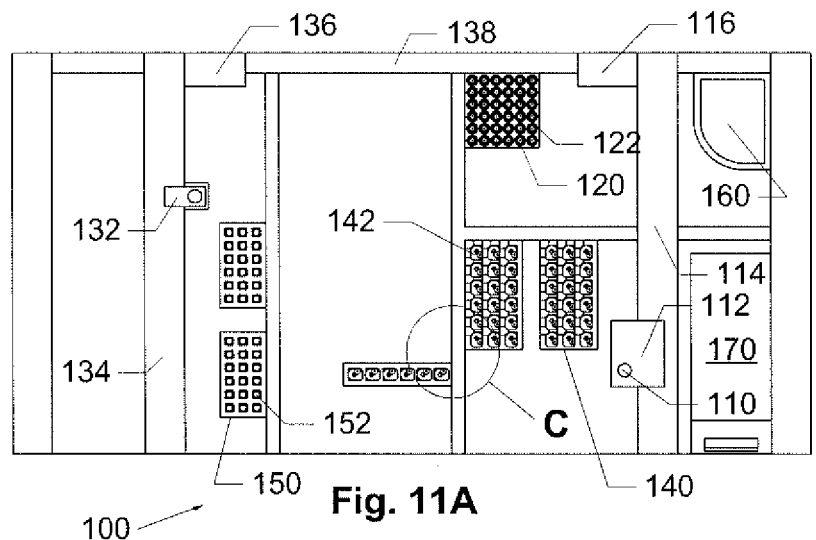
FIG. 11A is a schematic drawing showing details of a top view of a workstation 100 for automatically preparing sample ultra-filtrate from a sample.
Figure 11B:
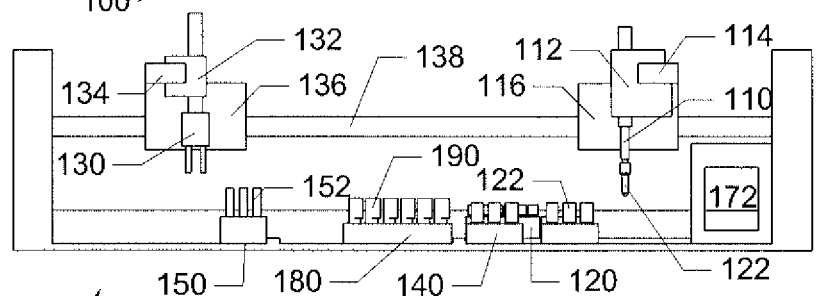
FIG. 11B is a top view of the workstation 100 shown in FIG. 11A.
Figure 11C:
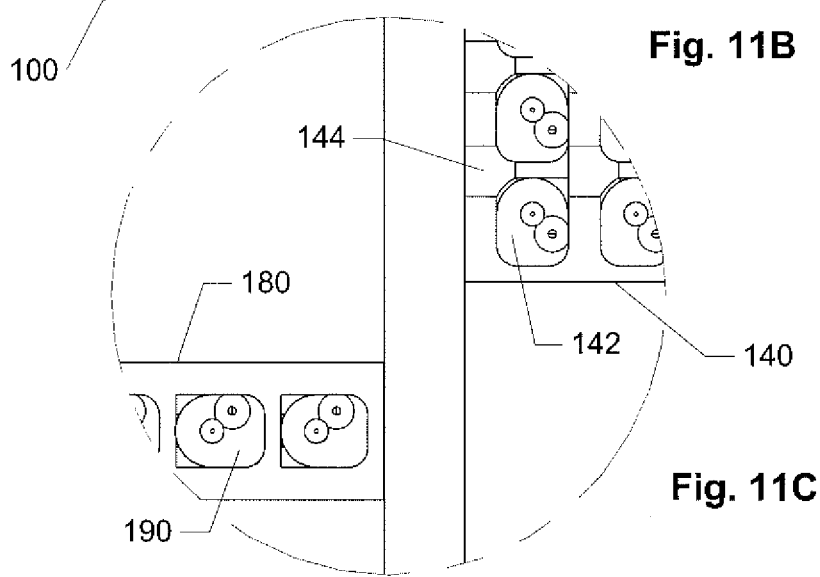
FIG. 11D is a detailed view of detail C shown in FIG. 11B showing details of ultra-filtration cartridges in an ultra-filtration cartridge rack, and ultra-filtration cartridge reservoir containing sample ultra-filtrate, in an analyzer sector for presenting sample ultra-filtrate to the analyzer.
FIG. 11E is a second perspective view of the workstation 100 shown in FIG. 11A.
Figure 11D:
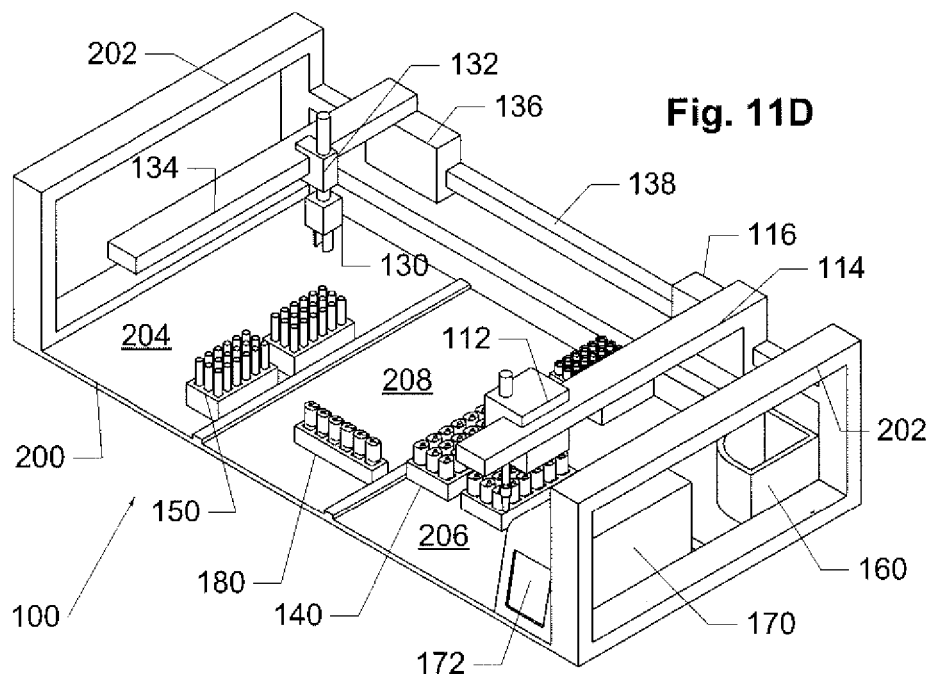
Figure 11E:
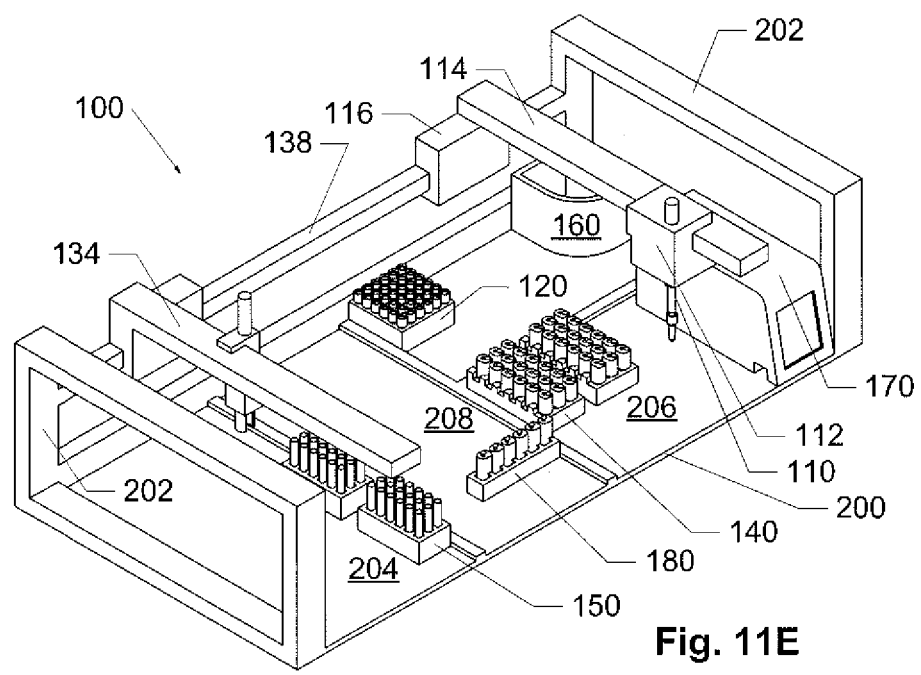

Still referring to FIGS. 3B, 3D, 3E, and 3F, the pipetting tip 70 operates in cooperation with a pipetting tool 110 shown in a workstation 100 illustrated in FIG. 11E. Details are not shown, but the pipetting tool 110 comprises resilient fingers that open radially by movement against the force exerted by a spring, whereby the resilient fingers can grab the pipetting tip piston gripping stem 89 up to and not beyond the pipetting tip piston flange upper face 91. An outer sleeve of the pipetting tool surrounding the resilient fingers frictionally engages the pipetting tip recess 77, enabling the pipetting tool 110 to move the pipetting piston 87 inside the pipetting tip housing 73 in a fluid-tight manner. By pushing the piston flange lower face 93 against the pipetting tip housing piston flange stop (inclined interior wall of pipetting tip housing) 83, and both the pipetting tip housing 73 and the pipetting tip piston 87 can be ejected into a waste container, as directed by a controller 170 that works in cooperating with the pipetting tool 110 (see workstation 100 shown in FIGS. 11D and 11E).

Referring to FIG. 1E, the pipetting tip 70 containing sample is inserted through the opening 43a into the cavity 45a, and sealably engages the filtration chamber inlet 47a. Force is applied to the piston 87, simultaneously forcing sample into the filtration chamber and compressing the air in the dead-end channel 51. After relaxing the force on the piston 87 to a predetermined level, the compressed air in the dead-end channel 51 reverses the flow of retentate. By repeating this piston force-release cycle, a forward and backward flow of sample across the surface of the membrane 67a is created, and trans-membrane pressure is created as well, causing ultra-filtrate to accumulate on the filtrate side of the membrane 35a. The vent 31a facilitates flow of ultra-filtrate into the bottom cavity of an ultra-filtrate reservoir 41a. The forward and backward flow of retentate across the membrane is a means for continuously washing the retentate side of the membrane and unplugging the membrane pores. The amount of ultra-filtrate that accumulates in the reservoir 41a is proportional to the number of piston force-release cycles.

Referring collectively to FIGS. 3A-3H and FIGS. 4A-4M, shown is a second embodiment of a disposable ultra-filtration cartridge 40 for automatic preparation of sample ultra-filtrate. Cartridge 40 is similar to cartridge 20 and accordingly, elements common to both cartridges share common reference numerals, but the letter "b" appended at the end of reference numerals to indicate a different embodiment; the letter "a" is used for cartridge 20. The pipetting tip 70 was previously described when cartridge 20 was described. A first difference between cartridge 40 and cartridge 20 are that the filtration membrane assembly 60b shown in FIGS. 4D and 4K are very different, and details of the filtration membrane assembly 60b are shown collectively in FIGS. 5A-5J. A second difference is that the opening 43b for allowing pipetting tip 70 to access the inlet 47b of the filtration chamber is substantially concentric with the circular shape of the cartridge along a horizontal plane. The implication is that in operation, the cartridge 40 does not have to be in any particular orientation (with respect to the X-Z and Y-Z planes) in the ultra-filtration cartridge rack 140 shown in FIG. 11E and FIG. 12D in the workstation 100 shown collectively in FIGS. 11A-11E, which shows a cartridge 142. Cartridge 142 is very similar to cartridge 20, in that the opening 43a is offset from the central vertical axis, and therefore the cartridges 142 have to be aligned with the programmed positions of the pipetting tool 110. In other words, opening 43a and 27a shown in FIGS. 1A and 1G are not aligned with each other. In contrast, opening 43b (see FIG. 3G) and opening 27b (see FIG. 3H) are substantially concentric.

Still referring collectively to FIGS. 3A-3H, and FIGS. 4A-4M, a third difference between cartridge 20 and 40 is that cartridge 40 comprises an upper section 30 frictionally engaged with a lower section 10. The upper section 30 comprises the filtration chamber, and the lower section is the ultra-filtrate reservoir with bottom cavity 41b. After processing a sample, upper section 30 is automatically removed with a gripping tool as for example, a gripping tool 130 shown in the workstation 100 (see FIGS. 11A & 11D). The remaining ultra-filtrate reservoir 10 containing ultra-filtrate is presented to an analyzer, like for example, analyzer 300 shown in FIGS. 12A-12C. As mentioned previously, some cartridges are shown in pieces, so that the individual pieces can be manufactured and then assembled. The upper section 30 of cartridge 40 is shown as pieces 30' and 30". The lengths of the upper section 30 and lower section 10 are sufficient to allow removal of section 30 and allow presentation of an ultra-filtrate in section 10 to an analyzer.

Referring collectively to FIGS. 4A-4M, various pieces of the cartridge are hidden sequentially in order to reveal underneath the hidden sections of the cartridge, without having to view cross-sections. FIG. 4A shows a schematic drawing showing details of a top view of the ultra-filtration cartridge 40 used for preparing an ultra-filtrate according to the second embodiment of the ultra-filtration cartridge, comprising the upper section 30 shown in two parts 30' and 30", and the lower section 10, with section 30" at the top. FIG. 4B shows a front view of the cartridge 40 shown in FIG. 4A. FIG. 4C shows a top view of cartridge 40 shown in FIG. 4A, with parts 30" and lower section 10 hidden. FIG. 4D shows a front view of the cartridge 40 shown in FIG. 4C. FIG. 4E shows a top view of cartridge 40 shown in FIG. 4A, with parts 30", lower section 10 and filtration membrane assembly 60b hidden. FIG. 4F shows a front view of the cartridge 40 shown in FIG. 4E. FIG. 4G shows a schematic drawing showing details of a top view of an ultra-filtration cartridge 40 used for preparing an ultra-filtrate according to a second embodiment of the ultra-filtration cartridge, comprising the upper section 30 shown in two parts 30' and 30", and the lower section 10, with section 30' at the top. FIG. 4H shows a front view of the cartridge 40 shown in FIG. 4G. FIG. 4J shows a top view of cartridge 40 shown in FIG. 4G, with parts 30' and lower section 10 hidden. FIG. 4K shows a front view of the cartridge 40 shown in FIG. 4J. FIG. 4L shows a top view of cartridge 40 shown in FIG. 4G, with parts 30', lower section 10 and filtration membrane assembly 60b hidden. FIG. 4M shows a front view of the cartridge 40 shown in FIG. 4L. Details of the filtration membrane assembly 60b are shown collectively in FIGS. 5B-5J.

Referring collectively to FIGS. 5B-5J, the views of the filtration membrane assembly 60b are described. FIG. 5A shows a schematic drawing showing details of a front view of the filtration membrane assembly 60b shown in FIG. 4D and FIG. 4K. FIG. 5B shows a top view of the filtration membrane assembly 60b shown in FIG. 5A. FIG. 5C shows a bottom view of the filtration membrane assembly 60b shown in FIG. 5A. FIG. 5D shows a first perspective view of the filtration membrane assembly 60b shown in FIG. 5A. FIG. 5E shows a second perspective view of the filtration membrane assembly 60b shown in FIG. 5A. FIG. 5F shows a third perspective view of the filtration membrane assembly 60b shown in FIG. 5A. FIG. 5G shows a fourth perspective view of the filtration membrane assembly 60b shown in FIG. 5A. FIG. 5H shows a cross-sectional view of the filtration membrane assembly 60b shown in FIG. 5A along line H-H. FIG. 5J shows a detailed view of detail J shown in FIG. 5H showing a schematic representation of the membrane 67b.

Referring collectively to FIGS. 6A-3J, and FIGS. 7A-7T shown is a third embodiment of a disposable ultra-filtration cartridge 50 for automatic preparation of sample ultra-filtrate. Cartridge 50 is similar to cartridge 20 and accordingly, elements common to both cartridges share common reference numerals, but letter "c" appended at the end of reference numerals to indicate a different embodiment; the letter "a" is used for cartridge 20 and the letter "b" is used for cartridge 40. The pipetting tip 70 was previously described when cartridge 20 was described. A first difference between cartridge 50 and cartridge 20 are that the filtration membrane assembly 60c shown in FIGS. 7F and 7M are very different, and details of the filtration membrane assembly 60c are shown collectively in FIGS. 8A-8J. The second difference is regarding the dead-end channel 51a shown in FIG. 1E, which is depicted as a groove in the body of the cartridge 20. The dead-end channel 51c in cartridge 50 is depicted as a piece of tubing with a closed end 53c and the open end 49c inserted into the filtration chamber outlet 49c. As mentioned previously, the open end and the outlet are coincidental, hence the same indicia 49c. A piece of tubing performs the same function as a groove described previously for cartridge 20, and are both within the scope of the invention.

The disposable ultra-filtration cartridge 50 is depicted in three major pieces: 50', 50", and 50'''. FIG. 6A shows a schematic drawing showing details of a top view of an assembly comprising an ultra-filtration cartridge 50 according to a third embodiment of the ultra-filtration cartridge, engaged with a pipetting tip 70, used for preparing an ultra-filtrate. FIG. 6B shows a right side view of the assembly comprising the cartridge 50 and the pipetting tip 70 shown in FIG. 6A. FIG. 6C shows a first cross-sectional view through the assembly comprising the cartridge 50 and the pipetting tip 70 shown in FIG. 6B along line C-C. FIG. 6D shows a perspective view of the cartridge 50 shown FIG. 6B and FIG. 6F. FIG. 6E shows a perspective view of the pipetting tip 70 shown FIG. 6B and FIG. 6F. FIG. 6F shows a front view of the assembly comprising the cartridge 50 and the pipetting tip 70 shown in FIG. 6A. FIG. 6G shows a second cross-sectional view through the assembly comprising the cartridge 50 and the pipetting tip 70 shown in FIG. 6F along line G-G. FIG. 6H shows a third cross-sectional view through the assembly comprising the cartridge 50 and the pipetting tip 70 shown in FIG. 6F along line H-H. FIG. 6J shows an enlarged of the cross-sectional view shown in FIG. 6H.

FIG. 7A shows a schematic drawing showing details of a top view of an ultra-filtration cartridge 50 used for preparing an ultra-filtrate according to a third embodiment of the ultra-filtration cartridge, shown in three parts 50', 50" and 50''', with the part 50''' at the bottom. FIG. 7B shows a front view of the cartridge 50 shown in FIG. 7A. FIG. 7C shows a top view of cartridge 50 shown in FIG. 7A, with front part 50''' hidden. FIG. 7D shows a front view of the cartridge 50 shown in FIG. 7C. FIG. 7E shows a top view of cartridge 50 shown in FIG. 7A, with the front part 50''' and the middle part 50" hidden. FIG. 7F shows a front view of the cartridge 50 shown in FIG. 7E. FIG. 7G shows a top view of the cartridge 50 shown in FIG. 7A, with the front part 50''', the middle part 50" and the and filtration membrane assembly 60c hidden. FIG. 7H shows a front view of the cartridge 50 shown in FIG. 7G. FIG. 7J shows a schematic drawing showing details of a top view of an ultra-filtration cartridge 50 used for preparing an ultra-filtrate according to a third embodiment of the ultra-filtration cartridge, shown in three parts 50', 50" and 50''', with the part 50' at the bottom. FIG. 7K shows a front view of the cartridge 50 shown in FIG. 7J. FIG. 7L is a top view of cartridge 50 shown in FIG. 7J, with back part 50' hidden. FIG. 7M shows a front view of the cartridge 50 shown in FIG. 7L. FIG. 7N shows a top view of cartridge 50 shown in FIG. 7J, with the back part 50' and the filtration membrane assembly 60c hidden. FIG. 7P shows a front view of the cartridge 50 shown in FIG. 7N. FIG. 7R shows a top view of the cartridge 50 shown in FIG. 7A, with the back part 50', the filtration membrane assembly 60c and the middle part 50" hidden. FIG. 7S shows a front view of the cartridge 50 shown in FIG. 7R. FIG. 7T is a cross-sectional view through the cartridge 50 shown in FIG. 7K along line T-T.

Regarding filtration membrane assembly 60c, FIG. 8A shows a schematic drawing showing details of a front view of the filtration membrane assembly 60c shown in FIG. 6F and FIG. 6M. FIG. 8B shows a top view of the filtration membrane assembly 60c shown in FIG. 8A. FIG. 8C shows a bottom view of the filtration membrane assembly 60c shown in FIG. 8A. FIG. 8D shows a first perspective view of the filtration membrane assembly 60c shown in FIG. 8A. FIG. 8E shows a second perspective view of the filtration membrane assembly 60c shown in FIG. 8A. FIG. 8F shows a third perspective view of the filtration membrane assembly 60c shown in FIG. 8A. FIG. 8G shows a fourth perspective view of the filtration membrane assembly 60c shown in FIG. 8A. FIG. 8H shows a cross-sectional view of the filtration membrane assembly 60c shown in FIG. 8A along line H-H. FIG. 8J shows a detailed view of detail J shown in FIG. 8H showing a schematic representation of the membrane 67c.

The filtration membrane assemblies 60a, 60b, and 60c for cartridges 20, 40, and 50 respectively comprise hollow fiber filtration membranes, wherein the outside represents the retentate side and the inside (lumen of the hollow fibers) represents the filtrate side. A person of reasonable skill in the art will appreciate that other membrane configurations can be used, and two other examples of membrane configurations are provided and referenced as 60d and 60e.

Filtration membrane assembly 60d also comprises hollow fiber filtration membranes, but the inside represents the retentate side and the outside represents the filtrate side. FIG. 9A shows a schematic drawing showing details of a top view of another embodiment 60d of a filtration membrane assembly. FIG. 9B shows a back view of the filtration membrane assembly 60d shown in FIG. 9A. FIG. 9C shows a front view of the filtration membrane assembly 60d shown in FIG. 9A. FIG. 9D shows a right side view of the filtration membrane assembly 60d shown in FIG. 9A. FIG. 9E shows a first perspective view of the filtration membrane assembly 60d shown in FIG. 9A. FIG. 9F shows a second perspective view of the filtration membrane assembly 60d shown in FIG. 9A. FIG. 9G shows a third perspective view of the filtration membrane assembly 60d shown in FIG. 9A. FIG. 9H shows a fourth perspective view of the filtration membrane assembly 60d shown in FIG. 9A. FIG. 9J shows a cross-sectional view of the filtration membrane assembly 60d shown in FIG. 9C along line J-J. FIG. 9K shows a detailed view of detail K shown in FIG. 9J showing a schematic representation of the membrane 67d.

Filtration membrane assembly 60e comprises a curved sheet of membrane. FIG. 10A shows a schematic drawing showing details of a top view of another embodiment 60e of a filtration membrane assembly. FIG. 10B shows a back view of the filtration membrane assembly 60e shown in FIG. 9A. FIG. 10O shows a front view of the filtration membrane assembly 60e shown in FIG. 10A. FIG. 10D shows a right side view of the filtration membrane assembly 60e shown in FIG. 10A. FIG. 10E shows a first perspective view of the filtration membrane assembly 60e shown in FIG. 10A. FIG. 10F shows a second perspective view of the filtration membrane assembly 60e shown in FIG. 10A. FIG. 10G shows a third perspective view of the filtration membrane assembly 60e shown in FIG. 10A. FIG. 10H shows a fourth perspective view of the filtration membrane assembly 60e shown in FIG. 10A. FIG. 10J shows a first cross-sectional view of the filtration membrane assembly 60e shown in FIG. 10B along line J-J. FIG. 10K shows a second cross-sectional view of the filtration membrane assembly 60e shown in FIG. 10O along line K-K. Other embodiments comprise one or more layers of flat membranes, and fluted membranes.

Referring collectively to FIGS. 11A-11E, shown is an automated workstation 100 for automatically preparing sample ultra-filtrates in disposable ultra-filtration cartridges. Although any disposable ultra-filtration cartridge similar to the ones described previously can be used, and therefore labeled 142, the cartridge 142 is very similar to the third embodiment ultra-filtration cartridge 50, illustrated collectively in FIGS. 6A-6J and FIGS. 7A-7T. FIG. 11A shows a schematic drawing showing details of a top view of a workstation 100 for automatically preparing sample ultra-filtrate from a sample. FIG. 11B shows a top view of the workstation 100 shown in FIG. 11A. FIG. 11C shows a detailed view of detail C shown in FIG. 11B showing details of ultra-filtration cartridges in an ultra-filtration cartridge rack, and ultra-filtration cartridge reservoir containing sample ultra-filtrate, in an analyzer sector for presenting sample ultra-filtrate to the analyzer. FIG. 11D shows a first perspective view of the workstation 100 shown in FIG. 11A. FIG. 11E shows a second perspective view of the workstation 100 shown in FIG. 11A.

The embodiment of a workstation 100 shown collectively in FIGS. 11A-11E has several features, but the features required in a workstation depend on for example, if the workstation is used as a stand-alone machine, and if the workstation is integrated in an automated laboratory. Moreover, there are features that are not shown that are present in some embodiments. As examples which should not be considered limiting in anyway, some of these features are: a) cartridge rack detectors for detecting the presence of a cartridge rack on the base at the predetermined locations; b) cartridge rack detectors output element for signaling the presence of a cartridge rack to the controller; c) sample tube rack detectors for detecting the presence of a sample tube racks on the base at the predetermined locations; d) sample tube rack detectors output element for signaling the presence of a sample tube rack to the controller; e) pipetting tip rack detectors for detecting the presence of a pipetting tip racks on the base at the predetermined locations; f) pipetting tip rack detectors output element for signaling the presence of a pipetting tip rack to the controller; g) rack position detectors; h) pins disposed on the base for enabling the different types of racks to be placed in the correct rack positions; i) sensors mounted slightly below the surface of the base in predetermined positions, which can be activated by providing the racks with magnets strong enough to activate the sensors; j) optical interrupters where a rack interrupts a light path; k) indicia reader for tracking the sample tubes, sample tube racks, ultra-filtration cartridges, ultra-filtration cartridge racks, ultra-filtration cartridge reservoirs containing sample ultra-filtrate, analyzer sectors for presenting sample ultra-filtrates to an analyzer, pipetting tip racks. Some examples of indicia, which should not be considered limiting in any way, include one-dimensional barcodes, a two-dimensional barcodes, and radio frequency identification tag attached to the sample tubes and the ultra-filtration cartridges. Many of these features are described in the prior art, for example U.S. Pat. No. 7,141,213.

Still referring collectively to FIGS. 11A-11E, shown in embodiment 100 of a workstation are a pipetting tool 110 for releasably holding a pipetting tip, a pipetting tool carriage 112 for supporting and cooperating with pipetting tool 110, a pipetting tool carriage movable arm 114 for supporting and moving pipetting tool carriage, a pipetting tip rack 120 for storing pipetting tips 70, a pipetting tool carriage movable arm carriage 116. On the left side of the workstation 100 is shown a gripping tool 130 for gripping for example, a sample tube or an ultra-filtration cartridge, to enable transportation thereof. Also shown are a gripping tool carriage 132 for supporting and cooperating with gripping tool, a gripping tool carriage movable arm 134 for supporting and moving gripping tool carriage, a gripping tool carriage movable arm 136, a track for facilitating movement of pipetting tool carriage movable arm carriage 116 and the gripping tool carriage movable arm 136 (shown as 138), an ultra-filtration cartridge rack 140, an ultra-filtration cartridge 142, a projected member 144 in the ultra-filtration cartridge rack, for enabling proper orientation of ultra-filtration cartridge with respect to X-Z and Y-Z planes, when the cartridge is located in the ultra-filtration rack for processing a sample. Also shown are, a sample tube rack 150, sample tube 152, a waste container 160 for receiving ejected used pipetting tip, a controller 170 for controlling the workstation, a controller data input element and display touch screen 172, a sample delivery site on the workstation for receiving samples in sample tubes contained in sample tube racks (204), an ultra-filtration cartridge rack site for on the workstation for housing ultra-filtration cartridges contained in ultra-filtration cartridge racks (206), and an analyzer sector site on the workstation for housing analyzer sectors (208).

Figure 12A:
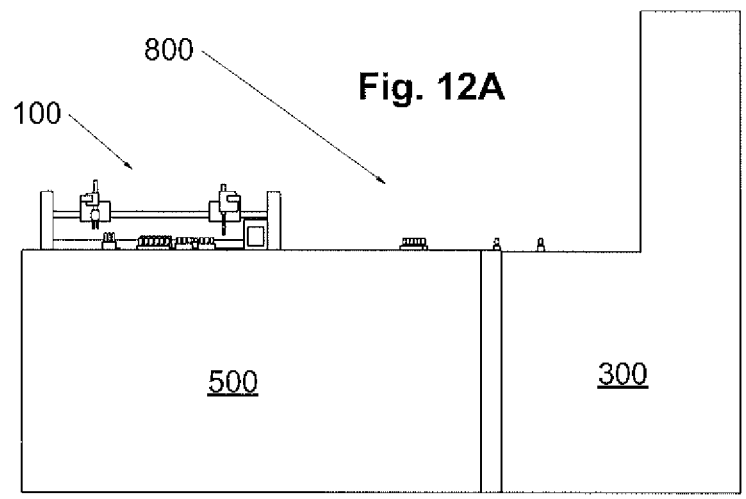
FIG. 12A is a schematic drawing showing details of a top view of an ultra-filtration system 800 for automatically preparing serum or plasma ultra-filtrate from a sample and presenting the ultra-filtrate to an analyzer for measuring free therapeutic drugs and hormones in serum or plasma.
Figure 12B:
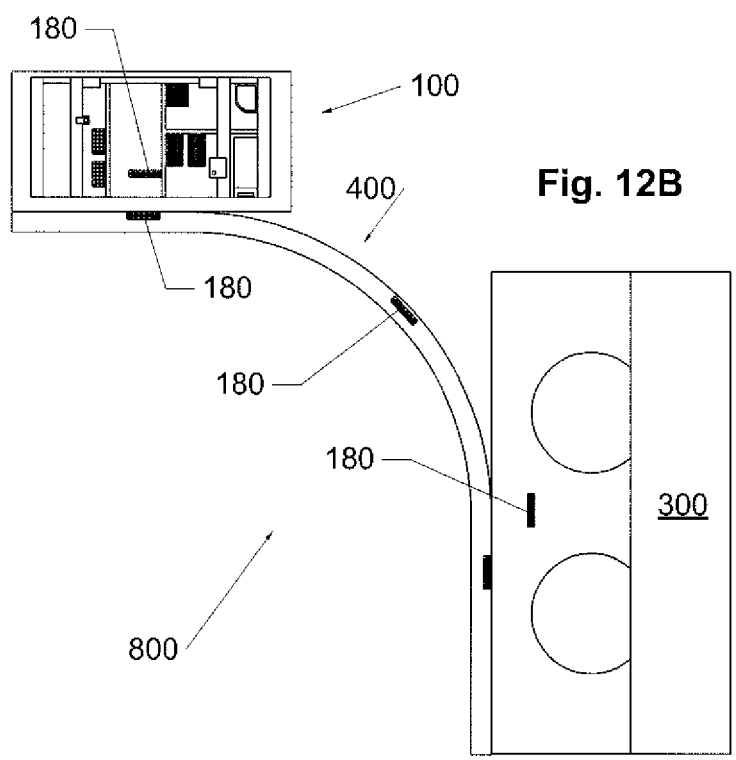
FIG. 12B is a top view of the system 800 shown in FIG. 12A.

Referring collectively to FIGS. 12A-12D, FIG. 12A shows a schematic drawing showing details of a top view of an ultra-filtration system 800 for automatically preparing serum or plasma ultra-filtrate from a sample and presenting the ultra-filtrate to an analyzer for measuring free therapeutic drugs and hormones in serum or plasma. FIG. 12B shows a top view of the system 800 shown in FIG. 12A. FIG. 12C shows perspective view of the system 800 shown in FIG. 12A. FIG. 12D shows a detailed view of detail D shown in FIG. 12C showing details of ultra-filtration cartridges 142 in an ultra-filtration cartridge rack 140, ultra-filtration cartridge reservoir containing sample ultra-filtrate 190 in an analyzer sector 180 for presenting sample ultra-filtrate to the analyzer, and ultra-filtration cartridge reservoir 190 containing sample ultra-filtrate in an analyzer sector 180 on a transport track 400 used to present the sample ultra-filtrate to the analyzer 300.

Referring to FIG. 12D and FIG. 11O, shown is a projected member 144 in the ultra-filtration cartridge rack 140, for enabling proper orientation of ultra-filtration cartridge with respect to X-Z and a Y-Z axes, when the cartridge is located in the ultra-filtration cartridge rack for processing a sample. This feature is not required with the second embodiment 40 of an ultra-filtration cartridge, which has a single opening at the top, having a center approximately concentric with the bottom of the cartridge. Therefore there is no concern that the pipetting tip will crash on the cartridge 40. However the concern with respect to the third embodiment of the cartridge 50, as shown in FIG. 12D, is addressed by, for example which should be considered limiting in any way, the projected members 144 between each holding position in the rack 140. In embodiments 20 and 50, the openings 27a and 27c respectively used by the analyzer probe for accessing sample ultra-filtrate, are approximately concentric with the bottom of the respective cartridge. Therefore when the ultra-filtrate is presented to an analyzer in ultra-filtrate reservoirs in any of the embodiment described, no orientation of the cartridge ultra-filtrate reservoirs with respect to X-Z or Y-Z planes is required.

While the above description provides example embodiments, it will be appreciated that the present invention is susceptible to modification and change without departing from the fair meaning and scope of the accompanying claims. Accordingly, what has been described is merely illustrative of the application of aspects of embodiments of the invention. Numerous modifications and variations of the present invention are possible in light of the above teachings. It is therefore to be understood that within the scope of the appended claims, the invention may be practiced otherwise than as specifically described herein. Furthermore, the discussed combination of features might not be absolutely necessary for the inventive solution.

REFERENCES CITED

1. U.S. Pat. No. 7,816,124
2. U.S. Pat. No. 7,807,450
3. U.S. patent application Ser. No. 13/549,443
4. U.S. Pat. No. 4,474,071
5. U.S. Pat. No. 7,141,213.

The invention claimed is:

1. A disposable ultra-filtration apparatus for automatic preparation of an ultra-filtrate from a sample, the apparatus comprising a disposable ultra-filtration cartridge and a disposable pipetting tip, the disposable ultra-filtration cartridge including
   a top end having a top face, the top face comprising at least one opening, the at least one opening providing an ultra-filtrate chamber vent;
   a bottom end for supporting the disposable ultra-filtration cartridge in an upright position in cooperation with a cartridge rack;
   a filtration chamber comprising (i) a membrane having pores of a predetermined pore size, and dividing the filtration chamber into a retentate volume on the retentate side of the membrane, and an ultra-filtrate chamber on the filtrate side of the membrane, (ii) a sample inlet directly connected to the retentate volume for sealably engaging the disposable pipetting tip containing the sample, (iii) a filtration chamber outlet directly connected to the retentate volume, (iv) the ultra-filtrate chamber vent directly connected to the ultra-filtrate chamber, and (v) an ultra-filtrate outlet directly connected to the ultra-filtrate chamber, wherein the ultra-filtrate chamber receives air through the ultra-filtrate chamber vent when the ultra-filtrate flows out of the ultra-filtrate outlet;
   a dead-end channel having an open end and a sealed end, wherein the open end is coincident with the filtration chamber outlet; and
   an ultra-filtrate reservoir at the bottom end for collecting the ultra-filtrate when the ultra-filtrate flows out of the ultra-filtrate outlet;
wherein
the disposable pipetting tip includes a piston movable in a first direction by applying a force to pressurize trapped air in the dead-end channel;
such that when the force is relaxed, the piston is movable in a second direction by the pressurized trapped air in the dead-end channel, the second direction being opposite to the first direction.

2. The disposable ultra-filtration apparatus according to claim 1, wherein the membrane in the filtration chamber comprises at least one hollow fiber membrane.

3. The disposable ultra-filtration apparatus according to claim 1, wherein based on the predetermined pore size, the heaviest substances passable through the pores of the membrane have a molecular weight that is less than about 30 kilodaltons, the pores of the membrane being impassible to substances heavier than about 30 kilodaltons.

4. The disposable ultra-filtration apparatus according to claim 1, wherein the ultra-filtrate chamber further comprises a first end and a second end; the first end being aligned with the at least one opening of the top face; and the second end being aligned with the ultra-filtrate outlet such that the at least one opening of the top face further provides direct access to the ultra-filtrate in the ultra-filtrate reservoir by an analyzer probe via the at least one opening of the top face.

5. The disposable ultra-filtration apparatus according to claim 4, wherein, in addition to the ultra-filtrate chamber vent being provided by the at least one opening in the top face, the opening in the top face also being configured to provide the direct access to the ultra-filtrate in the ultra-filtrate reservoir by the analyzer probe.

6. The disposable ultra-filtration apparatus according to claim 1, wherein the top end is detachably attachable to the bottom end.

7. The disposable ultra-filtration apparatus according to claim 6, wherein the top end is detachable from the bottom end to provide access to the ultra-filtrate in the ultra-filtrate reservoir by an analyzer probe.

8. The disposable ultra-filtration apparatus according to claim 1, wherein the at least one opening of the top face further provides access to the sample inlet of the filtration chamber by the disposable pipetting tip.

9. The disposable ultra-filtration apparatus according to claim 8, wherein, in addition to the ultra-filtrate chamber vent being provided by the at least one opening in the top face, the opening in the top face also being configured to provide the access to the sample inlet of the filtration chamber by the disposable pipetting tip.

10. The disposable ultra-filtration apparatus according to claim 1, wherein the dead-end channel accommodates a volume of air such that when the pressurized trapped air is depressurized, the volume of air is sufficient to provide a resulting reverse flow of sample across the surface of the membrane to release retentate caught in the pores of the membrane to the retentate side of the membrane across a substantial portion of the retentate side of the membrane.

11. The disposable ultra-filtration apparatus according to claim 1, wherein the disposable pipetting tip further comprises:
   a pipetting tip housing having a dispensing end, a gripping end, a recess disposed at the gripping end, and a pipetting tip housing piston flange stop, the piston being movable in a fluid-tight manner inside the pipetting tip housing, the piston having a piston sealing end proximal to the dispensing end, and a piston gripping stem distal to the dispensing end of the pipetting tip housing; and
   a pipetting tip piston flange having an upper face and a lower face;
   such that when the piston is fully inserted in the pipetting tip housing, the gripping stem of the piston is aligned with the gripping end of the pipetting tip housing.

* * * * *